US 6,696,499 B1

(12) United States Patent
Cohn et al.

(10) Patent No.: US 6,696,499 B1
(45) Date of Patent: Feb. 24, 2004

(54) METHODS AND COMPOSITIONS FOR REDUCING OR ELIMINATING POST-SURGICAL ADHESION FORMATION

(75) Inventors: Daniel Cohn, Jerusalem (IL); Eli Pines, Watchung, NJ (US); Anna Hotovely, Ashdod (IL)

(73) Assignee: Life Medical Sciences, Inc., Little Silver, NJ (US)

( * ) Notice: Subject to any disclaimer, the term of this patent is extended or adjusted under 35 U.S.C. 154(b) by 0 days.

(21) Appl. No.: 09/688,625

(22) Filed: Oct. 16, 2000

Related U.S. Application Data

(60) Division of application No. 08/890,802, filed on Jul. 11, 1997, now Pat. No. 6,136,333, which is a continuation-in-part of application No. 08/678,762, filed on Jul. 11, 1996, now Pat. No. 5,711,958.

(51) Int. Cl.[7] .......................... A61K 47/34; C08G 18/83; C08G 63/91; C08G 65/48
(52) U.S. Cl. ...................... 514/772.1; 525/424; 525/43; 525/449; 525/454; 525/408
(58) Field of Search .......................... 424/78.17, 78.36, 424/78.37; 525/424, 430, 449, 454, 468; 514/772.1

(56) References Cited

U.S. PATENT DOCUMENTS

| | | |
|---|---|---|
| 5,202,413 A | 4/1993 | Spinu |
| 5,319,059 A | 6/1994 | Redha et al. |

FOREIGN PATENT DOCUMENTS

| | | |
|---|---|---|
| EP | 0 295 055 A | 12/1988 |

*Primary Examiner*—Edward J. Webman
(74) *Attorney, Agent, or Firm*—Henry D. Coleman; R. Neil Sudol; William J. Sapone

(57) ABSTRACT

The present invention relates to a method for reducing adhesions associated with post-operative surgery. The present method comprises administering or affixing a polymeric composition preferably comprising chain extended, coupled or crosslinked polyester/poly(oxyalkylene) ABA triblocks or AB diblocks having favorable EO/LA ratios to a site in the body which has been subjected to trauma, e.g. by surgery, excision or inflammatory disease. In the present invention, the polymeric material provides a barrier to prevent or reduce the extent of adhesions forming.

11 Claims, No Drawings

METHODS AND COMPOSITIONS FOR REDUCING OR ELIMINATING POST-SURGICAL ADHESION FORMATION

This Application is a Division of Ser. No. 08/890,802 filed Jul. 11, 1997 now U.S. Pat. No. 6,136,333 which is a CIP of U.S. Ser. No. 08/678,762 filed Jul. 11, 1996 now U.S. Pat. No. 5,711,958.

The present invention relates to the discovery that the use of biodegradable polymeric compositions can prevent or reduce communication between two sites after surgery and thereby significantly reduce and in some cases, actually prevent post-operative adhesions which often occur during the initial phases of post-surgical repair.

BACKGROUND OF THE INVENTION

A major clinical problem relating to surgical repair or inflammatory disease is adhesion which occurs during the initial phases of the healing process after surgery or disease. Adhesion is a condition which involves the formation of abnormal tissue linkages. These linkages which form can impair bodily function, produce infertility, obstruct the intestines and other portions of the gastrointestinal tract (bowel obstruction) and produce general discomfort, e.g. pelvic pain. The condition can be life threatening. The most common form of adhesion occurs after surgery as a result of trauma, although adhesion may occur as a result of other processes or events such as pelvic inflammatory disease, mechanical injury, radiation treatment and the presence of foreign material.

Various attempts have been made to prevent postoperative adhesions. For example, the use of peritoneal lavage, heparinized solutions, procoagulants, modification of surgical techniques such as the use of microscopic or laparoscopic surgical techniques, the elimination of talc from surgical gloves, the use of smaller sutures and the use of physical barriers (films, gels or solutions) aiming to minimize apposition of serosal surfaces, have all been attempted. Unfortunately, very limited success has been seen with these methods. Barrier materials, in various forms such as films and viscous intraperitoneal solutions, which are designed to limit tissue apposition, have also met with only limited success. The best of these barrier materials include cellulosic barriers, polytetrafluoroethylene materials, and dextran solutions. Also, a number of films based on polylactic acid, polyglycolic acid and copolymers of the two have proven to be unsuccessful. Indeed, most barrier materials have met with failure because these materials can induce untoward biological effects, e.g., foreign body reaction.

U.S. Pat. No. 5,410,016 to Hubbell, et al. is directed to photopolymerizable biodegradable gels for use as adhesion barriers, as control release systems for drugs, to provide temporary protection of tissue surfaces and for adhering or sealing tissues together. Hubbell, et al. discloses water-soluble macromonomers containing photopolymerizable groups on each end which are administered or placed on tissues prior to a photopolymerization step. After administration, the macromonomers are photopolymerized in situ in order to produce a crosslinked polymer on the tissue. The method of Hubbell, et al. suffers from the disadvantage that it is a cumbersome system, requiring additional equipment and expertise which adds to the cost of the treatment. In addition, the method suffers from the disadvantage that the patient must be irradiated with energy to polymerize the macromonomers during or after surgery, potentially compromising sterility and complicating and prolonging the surgical process. Given the nature of the system used to polymerize macromonomers, the Hubbel system produces polymers of high crosslink density which are somewhat weak in structure. In contrast to the polymers of Hubbell, the present invention makes use of polymers which are polymerized prior to use in the patient ("prepolymerized").

Ideally, a physical barrier for adhesion prevention should be completely absorbable and nonreactive. In addition, it should stay in place in the body with a minimum of suturing or stapling.

OBJECTS OF THE INVENTION

It is an object of the present invention to provide polymeric barriers which may be used to substantially prevent tissue to tissue adhesions and adhesions between tissue and implants and devices.

It is an additional object of the invention to provide polymeric materials in film, other solid structures such as rods, cylinders, porous structures such as foams, dispersions, viscous solutions, liquid polymers, sprays or gels which may be administered easily and with uniform results after surgery.

It is a further object of the invention to provide polymeric materials which may be used to substantially prevent adhesions and which may be effective for delivering bioactive agents.

It is yet an additional object of the invention to provide bioabsorbable polymeric materials which can be produced in a variety of formulations which have acceptable strength, are non-reactive with patient tissue and are bioabsorbable.

It is yet another object of the present invention to provide polymeric barriers which can be used in various forms, e.g., films, other structures such as rods and cylinders, foams, gels, dispersions, liquid polymers, sprays or viscous solutions, to provide flexibility in administration and use.

These and/or other objects of the invention may be readily gleaned from the detailed description of the present invention which follows.

SUMMARY OF THE INVENTION

The present invention relates to a method for eliminating or reducing post-surgical tissue adhesions using polymeric materials which are substantially integral and relatively rapidly bioabsorbable. It is the combination of these characteristics in polymers of the present invention which has produced favorable results in substantially reducing or even eliminating post-operative adhesions. Moreover, the method of the present invention is performed simply and in a cost-effective manner without the need for additional or expensive equipment. Unlike the prior art methods, the present invention is used under sterile conditions without exceptional efforts to maintain sterility and avoids the necessity of irradiating the patient. In addition, certain polymers used in the present invention (e.g. films or related preformed structures of polymer) exhibit sufficient strength and flexibility to be able to conform to a site to be protected and allow a suture to hold a polymer structure in place at the site of surgery.

It now has been discovered that the polymers according to the present invention, which are able to generate an integral barrier, are advantageously employed in reducing and even completely eliminating post-surgical adhesions. The present method comprises administering or affixing to an area in a patient's body at risk for developing adhesions, a polymeric composition comprising AB diblocks (preferably, as di-diblocks, as discussed in greater detail herein) or ABA triblocks which are chain-extended, coupled and/or crosslinked. Preferably, the A blocks comprise aliphatic ester units, more preferably derived from hydroxy acid units or their cyclic dimers and the like, even more preferably α-hydroxy acid units. In many embodiments, the method comprises administering the instant polymer compositions to a site within the patient's body which has been subjected to surgical repair or excision. In the present invention, the polymeric material provides a barrier to prevent adhesions from forming. After this period of protection, the polymer will degrade and will be resorbed within the patient's body and/or excreted from the patient's body. According to the present method, problems associated with non-absorbtion or foreign body reactions are significantly reduced or prevented.

The polymer may be administered in various forms such as films, other structures including rods, cylinders, foams, dispersions, viscous solutions, liquid polymers, sprays or gels. The form a polymer takes at the surgical site will depend upon the type of surgery which has been performed or the condition which is to be treated and the site to be treated. In addition, the need to deliver the polymer to a particular site within the body may be determinitive of the form in which the polymer is delivered. The present method may be used after virtually any surgery to prevent tissue adhesion which occurs during the initial phases of post-surgical repair. Thus, in all applications where tissue is being repaired or excised, the polymers according to the present invention find utility to prevent adhesions. Generally, the polymers are used to prevent tissue to tissue adhesion and adhesions between tissues and implants or devices, which occur after surgical procedures, as well as other conditions, including certain disease states.

The present polymers preferably are based on polyester/poly(oxyalkylene) ABA triblocks or AB diblocks, where A is a polymer preferably comprising aliphatic ester units, which are preferably derived from hydroxy acid units or their cyclic dimers and the like, even more preferably α-hydroxy acid units or their cyclic dimers and the like, such as a related ester or lactone. Preferably the A block comprises α-hydroxyacid units derived from an aliphatic α-hydroxy carboxylic acid or a related acid, ester or similar compound such as, for example, lactic acid, lactide, glycolic acid, glycolide, or a related aliphatic hydroxycarboxylic acid or ester (lactone) such as, for example, β-propiolactone, ε-caprolactone, δ-glutarolactone, δ-valerolactone, β-butyrolactone, pivalolactone, α,α-diethylpropiolactone, ethylene carbonate, trimethylene carbonate, γ-butyrolactone, p-dioxanone, 1,4-dioxepan-2-one, 3-methyl-1,4-dioxane-2,5-dione, 3,3,-dimethyl-1-4-dioxane-2,5-dione, cyclic esters of α-hydroxybutyric acid, α-hydroxyvaleric acid, α-hydroxyisovaleric acid, α-hydroxycaproic acid, α-hydroxy-α-ethylbutyric acid, α-hydroxyisocaproic acid, α-hydroxy-α-methyl valeric acid, α-hydroxyheptanoic acid, α-hydroxystearic acid, α-hydroxylignoceric acid, salicylic acid and mixtures, thereof. The use of α-hydroxyacids in the present invention is preferred. The A block of the triblocks and diblocks used in the present invention preferably comprises a poly(α-hydroxy-carboxylic acid), for example, poly(glycolic acid), poly(L-lactic acid) and poly(D,L-lactic acid), because these polymers will degrade and produce monomeric units which may be metabolized by the patient. The B block in the triblocks used in the present invention is preferably a hydroxyl, carboxylic acid or amine terminated poly (oxyalkylene) block (preferably, hydroxyl terminated) and is more preferably either a poly(ethylene oxide) homopolymer or poly(ethylene oxide)-co-poly(propylene oxide) block copolymer.

The above triblocks or diblocks are preferably end-capped with hydroxyl groups and are chain-extended using difunctional chain extenders such as diisocyanates, dicarboxylates, diesters or diacyl halide groups in order to chain extend the triblocks into high molecular weight polymer chains. Alternatively, the triblocks may be end-capped with groups such as carboxylic acid moieties or ester groups (which may be reacted directly as ester groups, activated as "active" ester groups or converted to active acyl groups such as acyl halides) or isocyanate groups and then reacted with difunctional chain extenders such as diols, diamines, hydroxylamines, or polyoxyethylene (polyethylene glycol) or poly(ethylene oxide)-co-poly(propylene oxide) block copolymer chain extenders (especially, in the case of water soluble or water dispersible gels, dispersions or viscous solutions) among others, to produce chain extended polymers preferably having high molecular weight. It is the fact that the polymers according to the present invention preferably comprise chain-extended trimers, which have relatively high molecular weights, or dimers, which cover a range of molecular weights, provide polymeric characteristics which are advantageously employed in barriers of various forms including a preformed structure such as a film, rod, tube, bead, foam or ring or dispersions, sprays, gels, liquid polymers, viscous liquids and viscous solutions, among others, according to the present invention.

In certain aspects of the present invention, preferred polymers for use in the present invention have the following characteristics: they are prepolymerized, chain-extended, substantially non-crosslinked and biodegradable. In other instances, the polymers may be crosslinked. Preferred polymers are also non-reactive, i.e., they do not produce an unintended or adverse tissue reaction. The present polymers are advantageously used as barrier materials to reduce or prevent adhesion. Polymers used in various preformed structures such as films according to the present invention are sufficiently flexible to enable the polymer to substantially conform to the surface of the tissue to be treated, yet at the same time have sufficient strength to function as an integral and therefore, effective barrier to allow suturing the material to tissue. Polymers used in other forms such as gels, dispersions and viscous solutions according to the present invention also have sufficient structural integrity to be delivered to a site within the body and prevent adhesions at the same time that the polymers are water soluble and/or water dispersible in order to be delivered.

In the present invention, PELA is the generic name used to denote the preferred polymers comprising poly(ethylene oxide) and poly(lactic acid) blocks, being chain extended with a diisocyanate, most preferably hexamethylene diisocyanate. PELA polymers are generally designated with respect to their composition by the average molecular weight of the poly(ethylene oxide) chain and by their (EO/LA) ratio, where EO is the number of ethylene oxide units present and LA is the total number of lactoyl units (ester units) present. A general definition of EO/LA ratio is presented hereinbelow.

In the present invention, the ABA triblock is preferably a substantially non-water soluble unit comprising poly (hydroxy acid) blocks and poly(oxyalkylene blocks), preferably poly(α-hydroxy acid) blocks and ethylene glycol, diethylene glycol and poly(ethylene oxide) chains or poly (ethylene oxide)-co-poly(propylene oxide) block copolymers. The A block of the ABA triblocks of the present polymers is biodegradable and ranges in size from one monomeric unit (a monomeric unit within the A block being considered lactic acid, glycolic acid or a related hydroxy acid (ester) unit even where lactide and/or glycolide or related reactants containing more than one hydroxyacid unit are used to produce the A block) up to about 400 or more monomeric units, with a preferred size ranging from about 4 to about 50 units, more preferably about 6 to about 30 units, even more preferably about 8 to about 16 monomeric units, which length depends upon the length or molecular weight of the B block combined with the A block in triblocks according to the present invention. It is to be noted that the size of the A block may well fall outside of the above range, depending upon the overall physical characteristics of the ABA triblock formed and the size of the B block.

The A block is derived preferably from an α-hydroxy acid as described above, more preferably from units of glycolic acid, lactic acid (preferably L or D,L mixtures to promote bioabsorbability) or mixtures thereof, in the form of glycolide or lactide reactants (as explained in greater detail hereinbelow). In the final polymers to be used to reduce or prevent post-operative adhesion, the A blocks tend to create hard domains in the matrix and generally provide strength and structural integrity to the polymer. The A block is non-water soluble and is sized in combination with the more water soluble/water dispersible B block in order to preferably promote phase separation between the the A and B blocks in the ABA triblock and the final polymer to be used to prevent or reduce adhesions. Thus, the A block instills the final polymer with essential structural characteristics, which, in combination with the B block, results in a polymer which has excellent anti-adhesion characteristics (believed to be instilled by the B block) in combination with strength, structural integrity and biodegradability instilled by the A block. In addition, in certain embodiments according to the present invention, the length of the A block is believed to be important for providing a material with a phase separated microstructure.

The B block preferably comprises poly(ethylene oxide) or poly(ethylene oxide)-co-poly(propylene oxide) block copolymers and other PEO-rich chains which fall in the molecular weight ($M_w$) range as defined hereinbelow. The B block may preferably vary in size from about 100 Da (dalton units) up to about 200,000 Da or higher, with a more preferred range of about 400 Da up to about 20,000 Da. Even more preferably, the B block is a poly(ethylene oxide) ranging in size from about 400 to about 10,000 Da. Based upon the teachings of the present invention, one of ordinary skill will now know to vary the length of the B block and the A block to provide polymers having excellent anti-adhesion properties, depending upon the type of final formulation desired and its delivery characteristics.

The ABA triblocks or AB diblocks according to the present invention are generally described according to the length (number of monomeric repeating units) of the B block [preferably, poly(ethylene oxide), the repeating unit being in this case ethylene oxide units] divided by the total number of monomeric units in both A blocks (preferably, an α-hydroxy acid such as lactic acid) of the ABA triblock or the A block of the AB diblock. This ratio is referred to as the EO/LA ratio. Polymers comprised of ABA triblocks or AB diblocks which are chain extended, coupled or crosslinked pursuant to the present invention also may be described in terms of an EO/LA ratio for the polymer, in which case the EO/LA ratio simply represents the ratio of oxyalkylene units to monomeric units in the entire polymer. The EO/LA ratio of the entire polymer may be determined by NMR analysis. These polymers may also be designated with respect to their composition by the average molecular weight of the poly (ethylene oxide) (PEG) chain or chains and by the weight percentage of the PEG chain or chains in the triblock, diblock or total polymer. It should be noted, however, that in instances where the chain extender, coupler or crosslinking agent comprises a poly(ethylene oxide) chain, the EO/LA ratio for the polymer may vary considerably from the EO/LA ratio found in the ABA triblock or AB diblock (the total amount of EO may become considerably larger because of contribution of EO from the chain extender, and consequently, the EO/LA ratio for the polymer may be considerably larger than it is for the ABA triblock or AB diblock). Likewise, the weight percentage of PEG found in such a polymer may also be quite different from that found in the ABA triblock or AB diblock.

Without being limited by way of presentation, the concept of the EO/LA ratio may be exemplified by a polymer described as a poly(ethylene oxide)-lactic acid block copolymer (PELA) 6,000/3.8, which is a hexamethylene diisocyanate chain extended ABA triblock copolymer comprising PEG chains having an average molecular weight of 6,000 and an EO/LA ratio of 3.8. The triblock in this polymer comprises, therefore, a 6,000 molecular weight PEG segment for the B block containing approximately 136 ethylene oxide units and two A blocks each containing, on average, approximately 18 LA units. Alternatively, the same polymer can be designated as 6,000/69.8%, where 6,000 is the average molecular weight of the PEG chains, and 69.8% is the weight percentage of PEG in the ABA triblock. For this PELA 6,000/3.8 polymer, the molecular weight of the triblock is approximately 8592 (6,000 for the PEG chain and two poly (lactic acid) A blocks each having a molecular weight of approximately 1296, for a total for the two A blocks of 2592). The weight percentage of the PEG block in this triblock is, accordingly, 69.8% (6,000/8592).

Alternatively, by way of example, the ABA triblock described above may be chain extended with, for example, the following chain extender: HDI-PEG4000-HDI, which is formed by reacting a poly(ethylene oxide) chain of molecular weight 4000 with two moles of hexamethylene diisocyanate. The repeating unit, after reaction of this chain extender with the ABA triblock described in the paragraph above is $[(LA)_{18}\text{-PEG6000-}(LA)_{18}\text{-HDI-PEG4000HDI-}]$. The molecular weight of the triblock 8592 (6000+2×18× 72=2592) and that of the macrodiisocyanate chain extender is 2×168 (for the two HDI molceules)+4000 for the PEG chain. The MW of the repeating unit is therefore, 8592+ 4336=12928. The weight % of PEG in the repeating unit is 77.4% (6000+4000=10,000; 10,000/12928). In terms of the EO/LA ratio of the repeating unit, we have a total PEG MW of 10000, which comprises 10000/44 EO units=227.3 EO units. These units, divided by the 36 LA units present gives us a ratio of 6.3. Because it is difficult to define an average PEG MW in certain instances, since we could get, for the example above, an average MW of approximately 6000, which could be the result of PEG 10000 in the triblocks and 2000 in the chain extenders, or the result of simply having PEG chains of 6000 in each of the triblock and chain extender. The exemplary polymer we describe above is a PELA 6000/4000/77.4%.

The preferred EO/LA ratio for polymers according to the present invention ranges from about 0.1 to about 100 or more, preferably about 0.5 to about 30, more preferably from about 0.5 to about 10.0, more preferably about 1.0 to about 5.0, more preferably about 1.5 to about 4.5, even more preferably about 2.5 to about 3.5 and most preferably about 3.0. In certain instances, the EO/LA ratio may fall outside of these ranges, depending upon the final characteristics of the polymers which are desired. Preferred EO/LA ratios for individual polymers may also vary according to the size of the B block and the type of chain-extender which is used. In certain embodiments, as the size (molecular weight) of the B block in the triblocks increases, the preferred EO/LA ratio will tend to be somewhat less than in triblocks and polymers where the size of the B block is less.

Tailoring the properties of the antiadhesion barriers generated by the present polymers is based upon combining (a) the enhanced antiadhesion properties attributed, by way of theory, by the PEG (B block) segments; (b) the biodegradability of the polyester, preferably poly(hydroxy acid) A blocks; and (c) the mechanical properties derived from the partially phase separated microstructure of the polymeric matrix.

The PEG (B block) content is related to the efficaciousness of the polymer as an antiadhesion barrier. Higher PEG content may give rise to greater antiadhesion activity, but with fast polymer degradation. Since there is a requirement for the barrier to stay in place separating the relevant tissues for a determined period of time, there is an optimal EO/LA ratio which combines maximum PEG content with the biologically required residence time. In agreement with these basic considerations, preliminary animal data indicate that polymers of the present invention comprising PEG chains of a 6,000 molecular weight and having an EO/LA ratio of approximately 3.0, display optimal properties as antiadhesion barriers.

Based upon the teachings of the present invention, one of ordinary skill in the art will now know to vary the length of the A block to the B block in a manner which provides polymers having excellent structural integrity, biodegradability and activity which substantially inhibits post-operative adhesion.

The polymers according to the present invention are prepolymerized, chain-extended and attain high molecular weight. The polymers may be non-crosslinked or crosslinked. In order to increase the molecular weight of the polymer produced, the end-capped ABA triblock or AB diblock (which may be end-capped with hydroxyl, amine or carboxylic acid groups) is chain-extended using difunctional compounds such as diisocyanate, dicarboxylic acid compounds or derivatives of dicarboxylic acids such as diacyl halides. The product which is formed from the reaction of the chain extender or crosslinking agent with the ABA triblock or AB diblock according to the present invention will depend upon the chemical nature of the nucleophilic (or electrophilic) moieties on the ABA triblock or AB diblock (or related multi diblocks) and the electrophilic (or nucleophilic) moieties on the chain extender or crosslinking agent. The reaction products can vary widely to produce different moieties, such as urethane groups, ester groups, urea groups and amide groups, among numerous others. For example, in the case of an ABA triblock (hydroxyl terminated) reacting with diisocyanate chain extenders, the product is a urethane chain extended polymer. In the case of amine groups terminating the ABA triblocks reacted with diisocyanate chain extenders, the product is a urea. In the case of carboxylic acid groups terminating the ABA triblocks (which can be converted to anhydrides or acyl halides) reacting with an amine terminated chain extender or crosslinking agent, the product is an amide. Preferably, the nucleophilic end-capped triblocks are chain-extended with diisocyanate compounds in order to produce chain-extended polymers according to the present invention, although the chemical approaches, as explained above, may vary greatly. In the case of structures such as films, the chain extenders are used to provide greater molecular weight to the triblocks, thus enhancing structural integrity. In the case of gels, liquid polymers and/or viscous solutions, the chain extenders or crosslinking agents provide not only high molecular weight, viscosity control and structural integrity, but also a degree of water solubility/dispersibility consistent with the solubility and/or dispersibility of these polymers in water and the delivery of these polymers to a site within the patient's body. Thus, the chain extenders may be used to provide a number of benefits without using the approach of shortening the A blocks, which may hamper the beneficial morphological and mechanical effect.

The final polymers according to the present invention may be non-water soluble or in certain liquid, viscous solution and/or gel applications may absorb significant quantities of water. Certain polymers according to the present invention are water soluble, especially where the polymer has a high EO/LA ratio.

The polymers according to the present invention may be crosslinked in addition to being chain-extended. Crosslinking agents may be similar to the chain extenders used in the present invention, with the exception that the crosslinking agents contain at least three reactive functional groups, in contrast with chain extenders, which generally contain only two reactive functional groups.

The present invention therefore relates to polymer compositions and to methods of substantially reducing or preventing tissue adhesions in patients comprising exposing damaged tissue in a patient to a polymeric composition of the present invention in various forms, such as films, viscous solutions or gel forms, among numerous others. Depending upon the type of tissue to be treated, the extent of injury which has occurred, the nature of the surgical procedure performed and the way the polymer is administered, the polymeric composition according to the present invention may be used advantageously in different forms such as an integral film, a dispersion as well as a gel or a viscous solution. The present polymers may be used in conjunction with any type of surgical procedure, and in particular, intraabdominal, intraperitoneal or in pelvic surgery. More specifically, the present polymers may be used to substantially reduce or prevent adhesions in conjunction with musculoskeletal surgery, abdominal surgery, gynecological surgery, ophthalmic, orthopedic, central nervous system, cardiovascular and intrauterine repair.

DETAILED DESCRIPTION OF THE INVENTION

The following terms shall be used throughout the specification to describe the present invention.

The term "adhesion" is used to describe abnormal attachments between tissues or organs or between tissues and implants (prosthetic devices) which form after an inflammatory stimulus, most commonly surgery, and in most instances produce considerable pain and discomfort. When adhesions affect normal tissue function, they are considered a complication of surgery. These tissue linkages often occur between two surfaces of tissue during the initial phases of post-operative repair or part of the healing process. Adhesions are fibrous structures that connect tissues or organs which are not normally joined. Common post-operative adhesions to which the present invention is directed include, for example, intraperitoneal or intraabdominal adhesions and pelvic adhesions. The term adhesion is also used with reference to all types of surgery including, for example, musculoskeletal surgery, abdominal surgery, gynecological surgery, ophthalmic, orthopedic, central nervous system, cardiovascular and intrauterine repair. Adhesions may produce bowel obstruction or intestinal loops following abdominal surgery, infertility following gynecological surgery as a result of adhesions forming between pelvic structures, restricted limb motion (tendon adhesions) following musculoskeletal surgery, cardiovascular complications including impairing the normal movement of the heart following cardiac surgery, an increase in intracranial bleeding, infection and cerebrospinal fluid leakage and pain following many surgeries, especially including spinal surgery which produces low back pain, leg pain and sphincter disturbance.

The term "polymer" is used to describe compositions according to the present invention which are used to reduce and/or prevent adhesions. Polymers according to the present invention may range in molecular weight (average molecular weight) from about 1,000–3,000 to several million or more and as described, include oligomers of relatively low molecular weight.

The terms "poly(ethlyene glycol)", "poly(oxyethylene)" and poly(ethylene oxide) are used interchangably to describe the present invention. These polymers, of varying weights, are used in the B block of ABA triblocks and AB diblocks according to the present invention as well as in chain extenders and crosslinking agents which may also be used in the present invention. The terms "poly(oxyalkylene) containing" and "poly(ethylene oxide) containing" and are used to describe certain polymeric chains which contain at least some amount of poly(oxyalkylene) or poly(ethylene oxide). The terms "poly(oxyalkylene) rich" and "poly(ethylene oxide) rich" are used to describe certain polymeric chains containing at least 50% by weight (of the total weight of the polymeric chain described) poly(oxyalkylene) or poly (ethylene oxide).

The term "polyester" is used to describe polyester A blocks of ABA triblocks and AB diblocks used in polymeric compositions according to the present invention where A is a polymeric polyester unit which may be derived from an aliphatic hydroxy carboxylic acid or a related ester, lactone, dimeric ester, carbonate, anhydride, dioxanone or related monomer and is preferably derived from an aliphatic α-hydroxy carboxylic acid or related ester, such units derived from the following: including, for example, lactic acid, lactide, glycolic acid, glycolide, or a related aliphatic hydroxycarboxylic acid, ester (lactone), dimeric acid or related compound such as, for example, β-propiolactone, ε-caprolactone, δ-glutarolactone, δ-valerolactone, β-butyrolactone, pivalolactone, α,α-diethylpropiolactone, ethylene carbonate, trimethylene carbonate, γ-butyrolactone, p-dioxanone, 1,4-dioxepan-2-one, 3-methyl-1,4-dioxane-2,5-дione, 3,3,-dimethyl-1-4-dioxane-2,5-dione, cyclic esters of α-hydroxybutyric acid, α-hydroxyvaleric acid, α-hydroxyisovaleric acid, α-hydroxycaproic acid, α-hydroxy-α-ethylbutyric acid, α-hydroxyisocaproic acid, α-hydroxy-α-methyl valeric acid, α-hydroxyheptanoic acid, α-hydroxystearic acid, α-hydroxylignoceric acid, salicylic acid and mixtures, thereof. The use of α-hydroxyacids and their corresponding cylic dimeric esters, especially lactide and glycolide in the present invention, is preferred. It is noted that in using certain of the described monomers according to the present invention, the monomeric units which are produced are not specifically ester groups, but may include such groups as carbonate groups, urethane groups and related groups which are derived from the above-described monomers. It will be understood that the term polyester shall encompass polymers which are derived from all of the above monomers, with those which actually produce ester units being preferred.

The terms "poly(hydroxy carboxylic acid)" or "poly(α-hydroxy carboxylic acid)" are used to describe polyester A blocks of ABA triblocks or AB diblocks used in polymeric compositions according to the present invention where A is a polymeric polyester unit derived from an aliphatic hydroxy carboxylic acid or a related ester or dimeric ester and is preferably derived from an aliphatic α-hydroxy carboxylic acid or related ester, including a cyclic dimeric ester, such as, for example, lactic acid, lactide, glycolic acid, glycolide, or a related aliphatic hydroxycarboxylic acid or ester (lactone) such as, for example, ε-caprolactone, δ-glutarolactone, δ-valerolactone, γ-butyrolactone and mixtures, thereof, among numerous others as set forth herein. The use of α-hydroxyacids and their corresponding cylic dimeric esters, especially lactide and glycolide in the present invention, is preferred.

The term "triblock" is used to describe polymeric units which are used in certain embodiments to produce the polymers according to the present invention which comprise a first polyester A block covalently linked to a poly (oxyalkylene) B block as described above which is, in turn, covalently linked to a second polyester A block. Triblocks according to the present invention may be terminated by hydroxyl, amine, or carboxyl moieties, but in preferred embodiments, are terminated with hydroxyl groups which can be readily covalently linked to chain extenders, crosslinking agents or other groups which contain electrophilic moieties, to produce the final polymers which are used in the present invention.

The term "diblock" is used to describe polymeric units which comprise a first polyester A block [preferably, a poly(hydroxy carboxylic acid) polyester] covalently linked to a poly(oxyalkylene) B block as described above. In the present invention, diblocks may be formed, for example, by initiating a polymerization of hydroxy carboxylic acid (or equivalent monomeric, dimeric or related building blocks) with a hydroxyl, amine or carboxyl-terminated poly (oxyalkyelene) block which is end-capped (on one end of the polymer) with a non-reactive group (for example, an alkyl, aryl or aralkyl group or substituted alkyl, aryl or aralkyl group, preferably, a $C_1$–$C_{12}$ alkyl group or an equivalent, or a protecting group which can be removed to provide a free nucleophilic moiety at a later time). The diblocks which are produced may then be further reacted with chain-extenders, crosslinking agents and the like to produce polymers according to the present invention having favorable EO/LA ratios for use in reducing and/or preventing adhesion. Diblocks may be used in much the same way that ABA triblocks are used in the present invention, i.e., as building polymeric units of the polymers according to the present invention.

The term "multi-diblock" is used to describe compounds which contain units of diblocks which have been linked through chain extenders or couplers, in the case of diblocks, or crosslinking agents into a star-like or comb-like configuration.

The term "non-water soluble" or "substantially non-water soluble" is used to describe certain preferred ABA triblocks or AB diblocks used in various forms according to the present invention. In the present invention, in forms such as viscous solutions, gels or emulsions in which the polymers are substantially water soluble, the ABA triblocks or AB diblocks may be water soluble or non-water soluble. AB diblocks or multiblocks according to the present invention may be non-water soluble or water soluble. Non-water soluble triblocks or diblocks according to the present invention are soluble in water up to a limit of no more than about 0.5–0.6 g per 100 ml of water, preferably less than about 0.2 g per 100 ml of water. In determining water solubility, triblocks or diblocks according to the present invention are dissolved in, agitated or mixed in water at room temperature (i.e., at a temperature of about 20–23° C.) for a period of two hours. It is noted that in the present invention, chain extended triblocks which are used to produce structures such as films according to the present invention are also preferably substantially non-water soluble, i.e, they are limited in water solubility to no more than about 0.2 mg/ml. This limitation of water solubility reflects the fact that in certain embodiments according to the present invention, substantially non-soluble triblocks or diblocks which are preferably used in the present invention comprise at least about 25–30% by weight of A blocks.

An amount of the A blocks in the ABA triblocks or AB diblocks comprising at least about 25–30% by weight generally renders the triblocks or diblocks according to the present invention substantially non-water soluble. It is to be noted that water solubility or the absence of water solubility of the triblocks or diblocks may depend upon the molecular weight of the material. This characteristic is advantageous in the present polymeric compositions because the length and/ or size of the A block instills structural integrity and biodegradability to the final polymer, but also, by virtue of the relative hydrophobicity of the block, tends to reduce the water solubility of the ABA triblock or AB diblock. Consequently, polymeric compositions according to the present invention which contain a proper balance of A block or blocks to B block have a slow rate of biodegradability and consequently, a longer period of interaction with tissue to be protected from adhesion formation. This is reflected overall in the EO/LA ratio of the polymers according to the present invention.

Polymers to be used in viscous solutions, dispersions and/or gels according to the present invention are preferably water soluble and/or water dispersible and may use many of the same or similar ABA triblocks or AB diblocks used in polymeric structures such as films according to the present invention. In certain applications of the present inventions, in particular, in producing a liquid version which is substantially non-water soluble, having acceptable viscosity and flow characteristics for favorable administration, the polymers are actually substantially non-water soluble. Consequently, in applications such as films as well as in certain embodiments of the gel, dispersion and viscous solution applications, regardless of the way the polymers are administered, the ABA triblocks or AB diblocks which are preferably used are substantially non-water soluble. In certain alternative embodiments of the gels, dispersions and viscous solutions of the present invention, especially where the polymers are to be readily water dispersible, water solubility of the ABA triblocks or AB diblocks may be an advantageous characteristic, in which case, the inclusion of A blocks which comprise as little as about 1–5% by weight of the ABA triblocks or AB diblocks may be useful in the present invention.

The term "EO/LA ratio" is used to describe the relative amount of poly(ethylene oxide) or poly(ethylene oxide)-co-poly(propylene oxide) and ester units (such term including monomeric units which are not technically ester units, as described in greater detail herein but preferably, are hydroxy carboxylic acid units, even more preferably, α-hydroxy carboxylic acid units and most preferably, lactic acid units) which are used in ABA triblock or AB diblock copolymers and chain-extended polymers according to the present invention. This term refers to the length (number of monomeric units) of the B block [preferably, poly(ethylene oxide), the monomeric units being ethylene oxide units] divided by the total number of hydroxy acid (ester) units in both A blocks (preferably, lactic acid) of the ABA triblock or in the A block of the AB diblock as described hereinabove. Polymers comprised of ABA triblocks or AB diblocks which are chain extended pursuant to the present invention are also described in terms of an EO/LA ratio. The EO/LA ratio for polymers according to the present invention generally ranges from about 0.1 to about 100 or more, preferably ranges from about 0.5 to about 30 or more, more preferably from about 0.5 to about 10.0, more preferably about 1.0 to about 5.0, more preferably about 1.5 to about 4.5, even more preferably about 2.5 to about 3.5 and most preferably about 3.0. In certain instances, the EO/LA ratio may fall outside of these ranges, depending upon the final characteristics of the polymers which are desired. In the case of polymeric films, the EO/LA ratio preferably ranges from about 0.1 to about 25 or more, more preferably about 0.5 to about 10, even more preferably about 1.0 to 5.0, even more preferably about 1.5 to about 4.5 and even more preferably about 2.5 to 3.5, with about 3.0 within this range being particularly preferred. In the case of viscous solutions, dispersions and/or gels, the polymers may contain EO/LA ratios which range up to 30 or more. It is noted that in the case where a hydrophobic unit is used in the B block (for example a propylene oxide unit or higher alkylene oxide unit, this unit is considered as being a component in the denominator (LA) of the EO/LA ratio.

The term "prepolymerized" is used to describe the polymers according to the present invention which have been completely reacted before being introduced or administered to a patient to be treated. Prepolymerized polymers according to the present invention stand in contrast to polymers which may be polymerized in situ, i.e., at the site of administration in the patient. Prepolymerized polymers of the present invention are utilized to create both preformed strucrtures, e.g., compositions having three-dimensional structure such as films, cylinders, spheres, rods, blocks, tubes, beads, foam or rings, etc. and related structures, and non-preformed compositions such as sprays, gels, liquid polymers, viscous solutions and dispersions, among others.

The term "crosslinked" or "crosslinker" is used to describe agents which covalently bond the ABA triblocks or AB diblocks to other triblocks, diblocks or other moieties in the present polymers. As used herein, a crosslinker refers to a chemical compound which contains at least three (3) reactive moieties, for example, nucleophilic and/or electrophilic moieties, or moieties such as double-bonds, which can react through a radical initiated mechanism. In preferred embodiments, crosslinking agents according to the present invention have at least three of the same type of moieties, for example nucleophilic, electrophilic or radical-initiated moieties in order to facilitate the reaction of the crosslinker with triblocks and diblocks according to the present invention. In many respects, crosslinking agents are related to chain-extending agents in the present invention except that chain-extending agents contain only two reactive moieties, whereas crosslinking agents contain at least three reactive moieties. Exemplary crosslinking agents which can be used in the present invention include those which contain at least three isocyanate moieties, for example, isocyanurate, among numerous others, or a mixture of reactive moieties, such as carboxylic acid and hydroxylic groups (an example being citric acid or tartaric acid, among numerous others) and amine groups. One of ordinary skill in the art will be able to readily determine the type and amount of crosslinking agent which may be used in the present invention in order to facilitate the therapeutic method according to the present invention and the delivery of the polymers to a treatment site in a patient.

In the present invention reaction of an AB diblock with a crosslinking agent may produce a star molecule or, in other instances, different structures such as a comb polymer, for example, but not a crosslinked system per se. Inasmuch as the AB diblock will generally contain only one reactive moiety per molecule (except in the case where one of the two blocks contains a blocking group which may be removed and then reacted subsequent to the initial formation of the AB diblock), the use of crosslinkers will produce predetermined structures such as star or comb molecules. The inclusion or incorporation of an additional moiety in the diblock to which a crosslinking agent can react will generate a more elaborate crosslinked system akin to that produced with the ABA triblocks of the present invention.

The term "non-crosslinked", "substantially non-crosslinked", "crosslinked" or "substantially crosslinked" are used to describe the polymers according to the present invention which exhibit or display a substantial absence of crosslinking or, in other embodiments, substantial crosslinking. Polymers according to the present invention are advantageously associated with substantial post-surgical adhesion prevention or reduction. In certain embodiments, the present polymers actually prevent adhesions. Polymers according to the present invention which are considered substantially non-crosslinked preferably contain less than about 1.0% crosslinking, more preferably less than about 0.5% by weight crosslinking, even more preferably less than about 0.1% by weight crosslinking, most preferably less than about 0.05% by weight crosslinking are advantageously employed in the present invention. As used herein, reference to 1.0%, 0.5%, 0.1% etc. crosslinking refers to the amount by weight of a crosslinker which may be found in the polymers of the present invention. In other embodiments, polymers may be crosslinked, i.e., they may contain substantially more crosslinking agent than 1.0% by weight crosslinking agent.

The polymeric compositions according to the present invention are preferably chain-extended rather than crosslinked, but may be crosslinked in addition to being chain extended. It is also possible to produce crosslinked, non-chain extended polymers according to the present invention, but these polymers are generally crosslinked with more hydrophilic chain extenders in order to maintain a favorable EO/LA ratio. In certain preferred embodiments, the polymers are both chain extended and crosslinked. In the present compositions, chain extension provides the type of structural integrity and uniformity associated with the exceptional performance of the polymers of the present invention as anti-adhesion barriers. While not being limited by way of theory, it is believed that chain extension alone or in combination with crosslinking, in contrast to mere crosslinking with hydrophobic chain extenders without chain extension, allows a degree of mobility and flexibility of the hydrophilic B block which is consistent with anti-adhesion activity. The polymeric compositions according to the present invention provide an environment in which the A blocks (of the ABA triblock or AB diblock) will form hydrophobic, and often partially crystalline, hard microphases of high structural integrity and the B blocks will form hydrophilic, flexible phases, which are believed to be primarily responsible for good anti-adhesion activity. The formation of this microstructure, which is believed to be associated with polymeric compositions according to this invention and in particular, the flexibility of the PEG B blocks, produces excellent barriers for the reduction or prevention of post-surgical adhesions. Hydrophobic crosslinking of the triblocks according to the present invention without chain-extension (in contrast to hydrophilic crosslinking which may be used advantageously) not only limits molecular mobility, of special importance being its effect on the PEG segments, but also hampers or in certain instances, is believed to prevent microphase segregation from taking place. These two phenomena are believed to be associated with the production of less successful anti-adhesion barriers.

In general, crosslinking, especially if crosslinking density is high, prevents or at least substantially limits phase separation and to a greater extent, crystallization. In the present invention, the limitation of phase separation and crystallization will depend on the crosslinking density which is a function not only of the number of trimers which are crosslinked to those which are chain extended, but also on the molecular weight of the triblock and MW weight of its different components. In addition, the degree to which crosslinking will limit phase separation (and also crystallization) will depend on the molecular weight and flexibility of the crosslinker. Clearly, the shorter the crosslinker, the greater the decrease in molecular mobility and therefore, phase separation. The effect of the crosslinker being hydrophobic or hydrophilic on phase separation and molecular or segmental mobility is two-fold: a) hydration wil render the crosslinker more flexible and b) if the crosslinker is crystalline, its crystallinity will be destroyed by hydration. One is therefore, not limited to relatively low molecular weights of the crosslinker where, due to perturbations of the short chain, the polymer is unable to crystallize.

As used in the present invention, the ABA triblocks or AB diblocks used in the present polymers are preferably chain extended. The chain extenders which are used are difunctional compounds which react with the end-cap group of the triblocks to produce the chain extended triblocks according to the present invention. In the present invention, the amount of chain extender which is included within the polymers according to the present invention may vary. Thus, the molar ratio of chain extender to ABA triblock in the present polymers varies from about 0.5 to about 2.0 (about 1:2 to about 2:1, based upon the number of moles of difunctional chain extender and the number of moles of ABA triblock, more preferably about 0.8 to about 1.2 and most preferably about 1.0. In the case of diblocks, the preferred molar ratio of chain extender to to AB diblock varies from about 0.25 to about 1.0, with a more preferred ratio of about 0.5 to 1.0. When used with diblocks, the chain extenders are more accurately described as couplers, because they couple two diblocks together to form a di-diblock. It is noted that in synthesizing the present chain-extended polymers, the amount of chain extender which is reacted with difunctional triblock or diblock to produce polymer is generally slightly higher than the amount which is expected to be included in the final synthesized polymers.

Chain extenders which are used in the present invention, preferably contain no more than about 1% by weight of a crosslinking compound (such term signifying a compound containing at least 3 functional groups which can react with the end-cap group of the triblock and which generally appear in a chain extender sample as a side product of the synthesis or production of the chain extender), more preferably, less than about 0.5% by weight of a trifunctional compound and even more preferably less than 0.1% by weight. In certain embodiments, it is preferable to employ a difunctional chain extender which contains as little trifunctional (or higher functionality) compound as is practical. Also, the occurrence of side reactions which would lead to crosslinking of the polymers is negligible, due to both compositional as well as experimental parameters of the synthesis of the polymers of the present invention. Of course, in certain embodiments which separately employ crosslinking agents (either alone or in addition to chain extenders), the inclusion of weight percentages of crosslinking agents outside of the above-described weight ranges is within the scope of the present invention.

In the case of polymers which are used in structures such as films, the chain extenders are preferably non-water soluble. In the case of polymers which are used in systems such as water soluble gels, dispersions or viscous solutions, the chain-extenders are preferably highly water soluble. Preferred water soluble chain-extenders include, for example, polyethylene glycol diisocyanates or poly (ethylene oxide)-co-poly(propylene oxide) copolymer diisocyanates, with the polyethylene glycol or poly(ethylene oxide)-co-poly(propylene oxide) copolymer chain ranging in molecular weight from about 200 to about 20,000 or more with a preferred molecular weight ranging from about 600 to about 15,000, even more preferably about 600 to about 10,000. In cases where the preferred embodiment is a non-water soluble polymer in a liquid form, the chain extenders may also be substantially non-water soluble. The role of the chain extenders in the sgels and/or viscous solutions according to the present invention is to promote the water solubility/dispersibility of the polymers and affect their viscosity in an effort to provide polymers which are readily deliverable to a site in a patient's body and also to fine tune the kinetics of degradation, the dilution and/or the solubilization of these polymers, to obtain optimal residence time and enhance the performance of the polymer as a barrier between tissue planes.

In certain preferred embodiments according to the present invention, by utilizing chain extenders rather than crosslinking agents, the present polymers are substantially non-crosslinked, yet integral, and have the advantage of having excellent structural integrity and characteristics such as strength and flexibility, which are advantageous for producing an efficient barrier for preventing adhesions. Also its is believed that the present polymers substantially avoid the formation of particles or break-down products which occur in many of the prior art polymer compositions.

As an advantageous feature of the present invention, the polymers of the present invention are employed in the present invention to substantially reduce or prevent adhesions. While not being limited by way of theory, it is believed that the polymers according to the present invention which have a favorable EO/LA ratio allow greater mobility of polyoxyalkylene blocks (and in particular, polyethylene oxide blocks) within the ABA triblock or AB diblock used in the present invention, a condition which is believed to at least partially explain the favorable results obtained by the present polymers in substantially reducing or preventing adhesions. Chain extended polymers according to the present invention are more likely to enhance phase separation of the distinct A and B blocks which comprise the triblocks, a condition which is associated with the superior performance of the polymers of this invention as anti-adhesion barriers. It is preferred that the polymers of the present invention should be chain extended and substantially non-crosslinked, or chain extended and crosslinked while maintaining a favorable EO/LA ratio of the entire polymer as well as preserving flexibility and segmental mobility, as much as possible. Polymers which are simply crosslinked (without chain extension) are also useful in the present invention, provided that the crosslinking agent is substantially hydrophilic in composition and allows the retention of the required degree of flexibility and segmental mobility.

The term "integral" is used to describe polymers according to the present invention which are substantially non-permeable to mesenchymal cells, platelets, blood cells and other cells which are involved in the biology of adhesion formation. Integral polymers preclude cells which are involved in the adhesion process from crossing the polymer barrier and initiating the adhesion process. Integral polymers also exhibit favorable physical characteristics and mechanical properties consistent with substantially reducing or eliminating adhesions.

The term "chain extended" is used to describe polymers according to the present invention wherein the basic triblock or diblock is reacted with a difunctional chain extender to increase the molecular weight of the present polymers. In certain preferred embodiments, especially in the form of films, the present polymers are substantially non-crosslinked and are instead, chain-extended to provide sufficiently high molecular weight polymer chains to enhance the strength and integrity of the final polymer film compositions as well as affecting the rate of degradation. It is noted that chain extension of the polymers provides adequate stength and integrity of the final films and other structures, yet allows a degree of motility of the individual polyoxyalkylene B blocks within the ABA triblock or AB diblock in order to maximize the adhesion inhibiting characteristics of the films. In contrast, hydrophobically crosslinked polymers which are not chain extended, provide a more rigid structure which is believed to severely limit movement of the individual polymeric blocks Preferred chain extenders for use in the present invention include diisocyanates of the general formula:

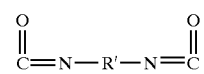

where R' is a $C_2$ to $C_{12}$, preferably a $C_2$ to $C_8$ alkylene group, a cycloalkyl or cycloalkyl-containing group, an aryl or aryl-containing group, 4,4'-diphenylmethane, toluene, naphthalene, 4,4'-dicyclohexylmethane, cyclohexyl, 3,3'-dimethylphenyl, 3,3'-dimethyl-diphenylmethane, 4,6'-xylylene, 3,5,5-trimethylcyclohexyl, 2,2,4-trimethylhexamethylene or p-phenylene. Equivalents of diisocyanates may also be used as chain extenders in the present invention. Addtional chain extenders may include macrodiisocyanates including isocyanate terminated poly (oxyalkylene) including isocyanate terminated polymers comprising poly(ethylene oxide) and polyethylene oxide)-co-poly(propylene oxide), among others.

Additional preferred chain extenders for use in the present invention include, for example, those according to the formula:

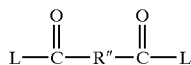

where R″ is a $C_0$ to $C_{12}$, preferably a $C_2$ to $C_8$, alkylene group or a hydroxyl or carboxylic acid substituted alkylene group, alkene, a cycloalkyl, hydroxyl or carboxylic acid-containing cycloalkyl or cycloalkyl-containing group, an aryl or aryl-containing group or a polyoxyalkylene chain comprised of poly(ethylene oxide), poly(ethylene oxide)-co-poly(propylene oxide) or other poly(ethylene oxide) rich chains and L is hydroxyl, a halide such as Cl, I or Br or an ester group which can be prepared from a hydroxyl group such as an alkyl, phenyl, benzyl or substituted alkyl, phenyl or benzyl group, including activated ester groups such as a tosyl group, mesyl group or related activating groups.

The term "biodegradable" relates to the characteristic whereby a polymer will degrade in the body. The polymers according to the present invention readily degrade in vivo and breakdown readily into monomeric units such as hydroxy acids. In the case of the PEG chains (B blocks), although these are not biodegradable, they are readily excreted by the patient upon degradation of the A block. The degradation of the present polymers mainly takes place through the hydrolysis of reactive bonds in the A block, such as aliphatic esters. The hydrolysis reaction is generally dependent upon pH. The rate constant for hydrolysis tends to be much higher at high pH (greater than 9.0) and low pH (less than 3.0) than at neutral pH (6.0 to 8.0). The rate constant for hydrolysis tends to be higher under basic conditions than under acidic conditions.

The A blocks of the triblocks and diblocks of the present polymers tend to be biodegradable, whereas the poly (oxyalkylene) B blocks of the triblocks, diblocks and chain extenders tend not to be biodegradable. In the case of water-soluble chain extenders and crosslinking agents which are preferably utilized in gels and viscous solutions according to the present invention, these chain extenders and crosslinking agents, which generally are highly water soluble, tend not to be biodegradable. In addition, when using polymers containing A blocks derived from α-hydroxy acids, the polymeric A blocks will degrade to individual α-hydroxy acids which are biosynthetically useful and may be involved in the patient's "biochemistry". In contrast, however, although the poly(oxyalkylene) polymeric B blocks are biocompatible, they are neither biodegradable nor bioabsorbable. Thus, in using the polymers according to the present invention it is recognized that the poly(oxyalkylene) blocks will remain as polymeric units in vivo until such time as the blocks are excreted. Consequently, the choice of an upper molecular weight range of the polyoxyalkylene block in the polymers according to the present invention will very much depend on the ability of the body to excrete or otherwise rid the body of the material.

The term "strength", "mechanical strength" or "sufficient suture-holding ablity" describes favorable mechanical and/or physical characteristics of the present polymers and reflects the fact that preferred polymers for use in the present invention (generally, as films) having a mechanical strength which is sufficient to allow a suture to be used to anchor the polymer to a tissue site without appreciable tearing or ripping of the film. These preferred polymers according to the present invention have an Ultimate Tensile Strength value preferably within the range of about 5–35 MPa and Elongation at Break values generally within the range of about 400–2000%.

The term "flexible" is used with respect to a physical description of the polymers of the present invention to reflect the fact that the present polymers are essentially non-rigid and non-brittle, and generally display an elastomeric behavior and tend to be conformable to a tissue surface to be treated. That is, the present polymers contain sufficient flexibility and are pliable enough to substantially conform to the contours of the tissue surfaces to be treated. Thus, polymeric compositions according to the present invention have a Young's Modulus preferably within the range of about 50–150 MPa.

The term "homogeneous" is used to describe preferred polymers according to the present invention. The term homogeneous is associated with the inclusion in the final polymer compositions of a population of triblocks and diblocks which are generally of the same size and preferably have a polydispersity of between about 1.0 and 2.0, more preferably about 1.1 to about 1.5 and even more preferably about 1.1 to about 1.2. Homogeneous triblocks and diblocks are associated with reproducible mechanical and physical characteristics and favorably consistent biodegradability.

The term "structure" is used to describe polymers according to the present invention which have form, size and dimensions which are established outside the body and will not significantly change upon being placed inside the body of the patient to be treated. The term structure embraces not only flat surfaced structures (i.e., films) in the traditional manner, but also cylinders, tubes and other three dimensional structures which are not substantially changed by the anatomy of the patient into which the structure has been placed.

The term "gels" is used to describe dispersions or suspensions of polymer which have been formed by dissolving, suspending or dispersing polymer in an aqueous solution for delivery to a site within the patient's body in order to prevent adhesions. Gels of the present invention typically contain polymer in a sterile aqueous solution (such solution comprising saline solution, sterile water or a water/ethanol mixture) at a viscosity ranging from about 100 to about 150,000 or more, preferably about 500 centipoise units up to about 50,000 centipoise units or more. More preferably, the gels are delivered in sterile, isotonic saline solution at a viscosity ranging from about 2000 centipoise units up to about 30,000 centipoise units depending upon the application. In certain aspects according to the present invention, liquid polymeric compositions comprising non-water soluble polymers may also be used.

Gels according to the present invention may be used in numerous applications to reduce or prevent adhesions, but preferably are employed to reduce or prevent adhesions following general surgical procedures and related surgeries which are minimally invasive. Gels utilize non-water soluble ABA triblocks which are chain extended with water-soluble or hydrophilic chain extenders in order to render the overall polymeric composition water dispersible or water soluble. Certain phases within the gel polymer compositions will be advantageously non-water soluble in order to promote the structural integrity and reduce the overall rate of biodegradability of the gel formulations in the body.

The term "viscous solution or suspension" is used to describe free-flowing solutions or suspensions of polymers according to the present invention wherein the solution has a viscosity which is greater than about 1 centipoise unit and less than about 60,000 or more centipoise units, more preferably about 1000 centipoise units to about 40,000 centipoise units or more, even more preferably about 2,000 centipoise units to about 20,000 centipoise units and above within this range. Viscous solutions or suspensions of polymers according to the present invention at viscosities approaching the high end of the range of viscosities may be indistinguishable from gels at the low end of a viscosity range. The present invention also contemplates liquid polymeric compositions having appropriate viscosity and flow characteristics and their use to reduce and/or prevent adhesions.

In the present invention, the ABA triblock or AB diblock is a unit which is generally comprised of ester units derived from a variety of monomers as described hereinabove and preferably comprises poly(hydroxy acid) polymers in the A block and poly(oxyalkyelene) polymers in the B block. The A block is however, substantially biodegradable and ranges in size from one monomeric unit up to about 400 or more monomeric units, with a preferred size ranging from about 4 to about 50 units, more preferably about 6 to about 30 units, even more preferably about 8 to 16 units. The A block preferably is derived from an alpha-hydroxy acid or a related ester or lactone which produces monomer units of alpha-hydroxy acid within the polymeric chain as will be described in greater detail below. More preferably the A block is derived from units of glycolic acid, lactic acid or mixtures thereof, in the form of glycolide or lactide reactants (dimeric α-hydroxy acids as explained in greater detail hereinbelow). The B block preferably comprises poly(ethylene oxide) or poly(ethylene oxide)-co-poly(propyleneoxide) block copolymers. In certain aspects of the present invention, for example, where a polymer comprises a sufficient weight percent of poly(ethylene oxide) units in chain extenders and/or crosslinking agents to instill the overall polymer with a favorable EO/LA ratio, the B block may be hydrophobic or hydrophilic and derived from, for example, diols, diamines and dicarboxylic acids, among other equivalent compounds.

Examples of such diol, diamine and diacarboxylic acid compounds include, for example, OH-terminated diol molecules such as ethylene glycol, butanediol, OH-terminated polycaprolactone chains ranging in molecular weight from several hundred up to several thousand or more (4,000+), poly(propylene glycol) also ranging in molecular weight from several hundred to several thousand or more (4000+), OH-terminated polyesters or oligoesters such as OH-terminated poly(ethylene succinate) or poly(hexamethyleneadipate) or polyfunctional diols such as tartaric acid (containing two OH groups which are reactive with isocyanates and two carboxylic acid groups, which, in carboxylate form, will function to enhance the overall hydrophilicity of the composition and can serve to provide a material with pH dependent water solubility). Additional examples of such compounds include amine-containing compounds (preferably, diamine) such as ethylene diamine, hexamethylene diamine, amino acids, such as lysine(where two amine groups react leaving an unreacted carboxylic acid group and oligopeptides (such term including compounds containig from one to 100 peptide units) with two reactive amino groups, among numerous others. Examples of difunctional carboxylic acid-containing compounds include, for example, succinic acid, sebacic acid, among numerous others, including adipic acid, succinic acid, malic acid, orfumaric acid, maleic acid, COOH-terminated polycaprolactone, COOH-terminated polyesters or oligoesters such as COOH-terminated poly(ethylene succinate) or poly(hexamethylene adipate). Additional examples of such compounds include, for example, C=C containing groups such as fumaric acid (trans) and maleic acid (cis), among others which react with the diisocyanates via their COOH groups which leave unreacted double bonds available for further derivation by different mechanisms. Indeed, a large number of molecules are able to start the polymerization step including polyaminoacids, saccharides, etc. One example may be a polymer where lactide dimer (LD) is not started by a PEG chain, but rather by butane diol. A pentamer will be formed with HDI and chain-extended using, for example, PEG 6000. Alternatively, one can generate the HDI-PEG6000-HDI macrodiisocyanate and react such a molecule with, for example, (LA)-BD-(LA)4 triblock to produce the material -(HDI)-(LA)-BD-(LA)4-HDI-PEG6000-. A huge number of alternative embodiments are contemplated by the present invention.

When such compounds are used to make AB diblocks, the difunctional diol, diamine or dicarboxylic acid compounds may be terminated with an unreactive or blocking group at one end of the compound, or, alternatively, the compound may simply be end-capped with an unreactive group such as an alkyl, cycloalkyl, aryl, aralkyl or related group. In such a case, the unreacted or blocked group may be "deblocked" thus producing an AB diblock which has reactive groups at the terminal end of the A block and at the terminal end of the B block. Alternatively, where the B block is simply end-capped with an unreactive group, the resulting AB diblock will have but one functional group at the terminal end of the A block, which can be chain-extended, coupled or crosslinked to multi-diblocks according to the present invention.

The B block may vary in size from about 100 Da (dalton units) up to about 200,000 Da or higher, with a preferred range of about 1,000 Da up to about 20,000 Da. Most preferably, the B block is a poly(ethylene oxide) ranging in size from about 3,000 to about 10,000 Da. It is unexpectedly found that the poly(ethyleneoxide) B block provides the greatest inhibition or reduction in adhesion in the present invention.

The ABA triblock or AB diblock is preferably end-capped with nucleophilic moieties such as hydroxyl or amine groups. Alternatively, these triblocks and diblocks may be end-capped with carboxylate groups as well. With the preferred nucleophilic end-capping groups in place, the ABA triblock or AB diblock may be readily chain extended using difunctional electrophilic compounds such as diisocyanate or dicarboxylic acid compounds (or derivatives of dicarboxylic acids such as esters or diacyl halides). More preferably, the triblocks or diblocks are end-capped with hydroxyl groups and chain extended with diisocyanate compounds in order to produce the preferred polymers according to the present invention.

The present invention therefore, relates to a method of substantially reducing or preventing tissue adhesions in patients comprising exposing damaged tissue in a patient to a polymeric composition in a structure such as a film, gel, dispersion, liquid polymer, spray or viscous solution form comprising a multiblock polymer according to the present invention. Structures such as films which incorporate the polymers according to the present invention are preferably characterized by their favorable flexibility, mechanical strength and suture-holding ability as well as being substantially non-water soluble, chain extended, integral and biodegradable. Other structures used in the present invention, as well as gels, viscous solutions and emulsions, incertain aspects, may be preferably water soluble. In all aspects according to the present invention, certain embodiments may be substantially non-water soluble or water soluble, depending upon a variety of factors which may be influenced by treatment and/or delivery of the present compositions to a site of activity.

Preferably, the molecular weight of triblocks, diblocks and polymers used in the present invention are relatively homogeneous which provides for advantageous characteristics in films and related structures, gels, dispersions, sprays, liquid polymers and solutions/emulsions.

Preferred polymers used in the present invention as films and other preformed structures which make use of ABA triblocks, in contrast to AB diblocks, are poly(α-hydroxycarboxylic acid)/poly(oxyalkylene) polymers of the chemical structure:

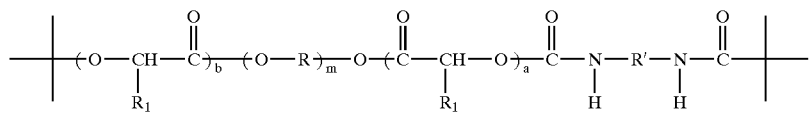

where a, b and m are positive integers, R is an ethylene and/or propylene group with the proviso that R is not exclusively a propylene group when R' contains an absence of poly(ethylene oxide), R' is a $C_2$ to $C_{12}$, preferably a $C_2$ to $C_8$ alkylene group, a cycloalkyl or cycloalkyl-containing group, an aryl or aryl-containing group, 4,4'-diphenylmethane, toluene, naphthalene, 4,4'-dicyclohexylmethane, cyclohexyl, 3,3'-dimethylphenyl, 3,3'-dimethyl-diphenylmethane, 4,6'-xylylene, 3,5,5-trimethylcyclohexyl, 2,2,4-trimethylhexamethylene, p-phenylene or a poly(ethylene oxide) containing or poly(ethylene oxide) rich chain and $R_1$ is H or $CH_3$. More preferably, R' is a hexamethylene group ($C_6$ alkylene group), R is an ethylene group and $R_1$ is $CH_3$. In preferred embodiments, the integers a and b are equal. In these preferred polymers, triblocks, rather than diblocks, are used.

Additional preferred polymers for use in the present invention as films and other preformed structures which make use of ABA triblocks, in contrast to AB diblocks, include those of the following structure:

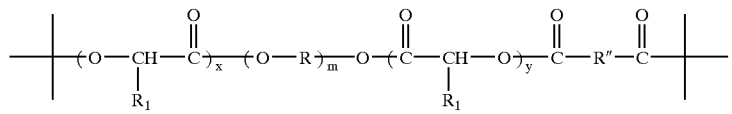

where x, y and m are positive integers, R is an ethylene and/or propylene group with the proviso that R is not exclusively a propylene group when R" contains an absence of poly(ethylene oxide), $R_1$ is a hydrogen or methyl group, R" is a $C_0$ to $C_{12}$, preferably a $C_2$ to $C_8$, alkylene group or a hydroxyl or carboxylic acid substituted alkylene group, alkene, a cycloalkyl, hydroxyl or carboxylic acid containing cycloalkyl or cycloalkyl-containing group, an aryl or aryl-containing group or a polyoxyalkylene chain comprised of poly(ethylene oxide), poly(ethylene oxide)-co-poly(propylene oxide) or other poly(ethylene oxide) rich chains. More preferably, R" is a $C_2$ to $C_4$ alkylene group, R is an ethylene group and $R_1$ is $CH_3$. The integers x and y are preferably equal.

The moiety

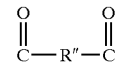

may be derived from numerous di- and tricarboxylic acids including, for example, citric acid, malic acid and tartaric acid, among numerous others such as oxalic acid, malonic acid, succinic acid, 2,3-dimethylsuccinic acid, glutaric acid, 3,3-dimethylglutaric acid, 3,3-dimethylglutaric acid, 3-methyladipic acid, adipic acid, pimelic acid, suberic acid, azelaic acid, sebacic acid, 1,9-nonanedicarboxylic acid, 1,10-decanedicarboxylic acid, 1,11-undecanedicarboxylic acid, 1,12-dodecanedicarboxylic acid, maleic acid, fumaric acid, diglycolic acid, hydromuconic acid, among others, including equivalents of these acids. These di- and tricarboxylic acids may be used to chain extend the ABA triblocks under controlled conditions so that crosslinking is substantially prevented. Alternatively, the use of the tricarboxylic acids may result in substantial crosslinking in certain aspects of the present invention. In the case of using dicarboxylic acids containing additional carboxylic acid groups and/or other polar groups such as hydroxyl groups, as in the case of citric acid or malic acid, among others, these will tend to enhance the water solubility of the final polymeric compositions.

Other embodiments according to the present invention relate to polymeric compositions which have the following general structure:

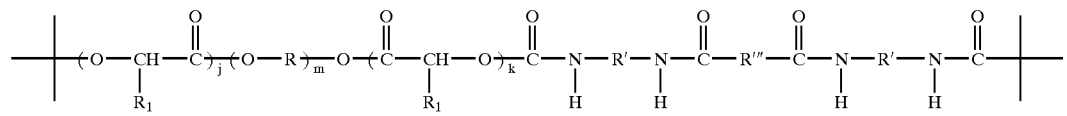

where j, k and m are positive integers, R is an ethylene and/or propylene group with the proviso that R is not exclusively a propylene group when R' and R''' contain an absence of poly(ethylene oxide), R' is a $C_2$ to $C_{12}$, preferably a $C_2$ to $C_8$ alkylene group, a cycloalkyl or cycloalkyl-containing group, an aryl or aryl-containing group, 4,4'-diphenylmethane, toluene, naphthalene, 4,4'-dicyclohexylmethane, cyclohexyl, 3,3'-dimethylphenyl, 3,3'-dimethyl-diphenylmethane, 4,6'-xylylene, 3,5,5-trimethylcyclohexyl, 2,2,4-trimethylhexamethylene, p-phenylene or a poly(ethylene oxide) containing or poly(ethylene oxide) rich chain, R''' is a polyoxyalkylene chain comprised of poly(ethylene oxide), poly(ethylene oxide)-co-poly(propylene oxide) or other poly(ethylene oxide) rich chains or a diol, diamine or dicarboxylic acid (an OH, $NH_2$, or COOH terminated molecule reactive with an isocyanate, in certain embodiments, preferably having at least one C=C containing molecule) or an ABA triblock wherein A is a polyester unit and B is a diol, diamine, dicarboxylic acid or a poly(oxyalkylene) containing or poly(oxyalkylene) rich chain and $R_1$ is H or $CH_3$. Examples of such compounds include, for example, OH-terminated diol molecules such as ethylene glycol, butanediol, OH-terminated polycaprolactone chains ranging in molecular weight from several hundred up to several thousand or more (4,000+), poly(propylene glycol) also ranging in molecular weight from several hundred to several thousand or more (4000+), OH-terminated polyesters or oligoesters such as OH-terminated poly(ethylene succinate) or poly(hexamethyleneadipate) or polyfunctional diols such as citric acid or tartaric acid (the latter containing two OH groups which are reactive with isocyanates and two carboxylic acid groups, which, in carboxylate form, will function to enhance the overall hydrophilicity of the composition and can serve to provide a material with pH dependent water solubility). Additional examples of such compounds include amine-containing compounds (preferably, diamine) such as ethylene diamine, hexamethylene diamine, amino acids, such as lysine(where two amine groups react leaving an unreacted carboxylic acid group and oligopeptides with two reactive amino groups, among numerous others. Examples of difunctional carboxylic acid-containing compounds include, for example, oxalic acid, succinic acid, malic acid, adipic acid, sebacic acid, orfumaric acid, maleic acid, COOH-terminated polycaprolactone, COOH-terminated polyesters or oligoesters such as COOH-terminated poly(ethylene succinate) or poly(hexamethylene adipate). Additional examples of such compounds include, for example, C=C containing groups such as fumaric acid (trans) and maleic acid (cis) which react with the diisocyanates via their COOH groups, leaving the unreacted double bond available for further derivation by different mechanisms. More preferably, R' is a hexamethylene group ($C_6$ alkylene group), R is an ethylene group, R''' is poly(ethylene oxide) and $R_1$ is $CH_3$. The integers j and k are preferably equal.

The present invention also relates to compositions for use in reducing or preventing adhesions in a patient comprising a polymer of the chemical structure:

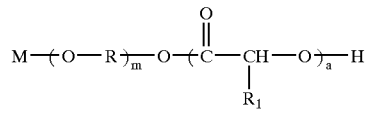

where m and a are positive integers,

R is an ethylene group and/or propylene group with the proviso that R is not exclusively a propylene group, $R_1$ is H or $CH_3$ and M is a non-reactive group, preferably a group selected from a $C_1$ to $C_{12}$ alkyl group, an aryl group, an aralkyl group or a substituted $C_1$ to $C_{12}$ alkyl group, aryl group, aralkyl group or a blocking group. Preferably, $R_1$ is $CH_3$.

The present invention also relates to a composition for use in reducing or preventing adhesions in a patient comprising a polymer of the chemical structure:

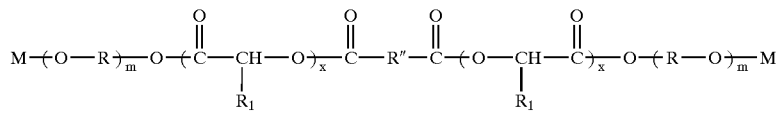

where m and x are positive integers,

R is an ethylene group and/or propylene group with the proviso that R is not exclusively a propylene group when R'' contains an absence of poly(ethylene oxide), M is a non-reactive group, R'' is a $C_0$ to $C_{12}$ alkylene group or a hydroxyl or carboxylic acid substituted alkyl group, a cycloalkyl, a hydroxyl-containing cycloalkyl, or cycloalkyl-containing group, an aryl or aryl-containing group, or a polyoxyalkylene chain-containing group comprised of poly(ethylene oxide), poly(ethylene oxide)-co-poly(propylene oxide) or a poly(ethylene oxide) rich chain, $R_1$ is H or $CH_3$ and M is a non-reactive group. Preferably, the non-reactive group is a $C_1$ to $C_{12}$ alkyl group, an aryl group, an aralkyl group or a substituted $C_1$ to $C_{12}$ alkyl group, an aryl group, an aralkyl group or a blocking group and more preferably, M is methyl or ethyl.

The present invention also relates to a composition for use in reducing or preventing adhesions in a patient comprising a polymer of the chemical structure:

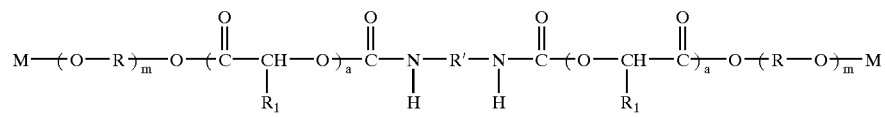

where m and a are positive integers,

R is an ethylene group and/or propylene group with the proviso that R is not exclusively a propylene group when R' contains an absence of poly(ethylene oxide), M is a non-reactive group, R' is a $C_2$ to $C_{12}$ alkylene group, a cycloalkyl or cycloalkyl-containing group, an aryl or aryl-containing group, 4,4'-diphenylmethane, toluene, naphthalene, 4,4'-dicyclohexylmethane, cyclohexyl, 3,3'-dimethylphenyl, 3,3'-dimethyl-diphenylmethane, 4,6'-xylylene, 3,5,5-trimethylcyclohexyl, 2,2,4-trimethylhexamethylene or p-phenylene or a poly(ethylene oxide) containing or poly(ethylene oxide) rich chain and $R_1$ is H or $CH_3$. Preferably, the non-reactive group is a $C_1$ to $C_{12}$ alkyl group, an aryl group, an aralkyl group or a substituted $C_1$ to $C_{12}$ alkyl group, an aryl group, an aralkyl group or a blocking group and more preferably, M is methyl or ethyl.

The present invention also relates to a composition for use in reducing or preventing adhesions in a patient comprising a polymer of the chemical structure:

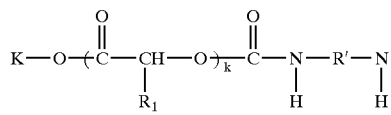

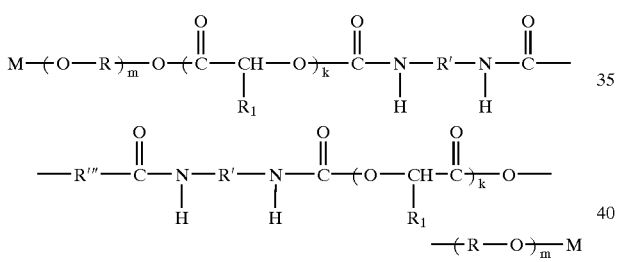

where m and k are positive integers,

R is an ethylene or propylene group with the proviso that R is not exclusively a propylene group when R' and R''' contain an absence of poly(ethylene oxide), R' is a $C_2$ to $C_{12}$ alkylene group, a cycloalkyl or cycloalkyl-containing group, an aryl or aryl-containing group, 4,4'-diphenylmethane, toluene, naphthalene, 4,4'-dicyclohexylmethane, cyclohexyl, 3,3'-dimethylphenyl, 3,3'-dimethyl-diphenylmethane, 4,6'-xylylene, 3,5,5-trimethylcyclohexyl, 2,2,4-trimethylhexamethylene, p-phenylene or a poly(ethylene oxide) containing or poly(ethylene oxide) rich chain, R''' is selected from the group consisting of poly(ethylene oxide), poly(ethylene oxide)-co-poly(propylene oxide), a poly(ethylene oxide)-rich chain, a diol, a diamine, a dicarboxylic acid and an ABA triblock, said diol preferably being selected from the group consisting of ethylene glycol, butanediol, OH-terminated polycaprolactone, poly(propylene glycol), OH-terminated polyester or oligoesters, tartaric acid, said diamine being preferably selected from the group consisting of ethylene diamine, hexamethylene diamine, amino acids, and oligopeptides and said dicarboxylic preferably being selected from the group consisting of succinic acid, sebacic acid, adipic acid, malic acid, oxalic acid, maleic acid, fumaric acid, COOH-terminated polycaprolactone, and COOH-terminated polyesters or oligoesters, wherein A is a polyester unit and B is selected from the group consisting of poly(ethylene oxide), poly(ethylene oxide)-co-poly(propylene oxide), a poly(ethylene oxide) rich chain, a diol, a diamine and a dicarboxylic acid, $R_1$ is H or $CH_3$ and M is a non-reactive group. Preferably the non-reactive group is a $C_1$ to $C_{12}$ alkyl group, an aryl group, an aralkyl group or a substituted $C_1$ to $C_{12}$ alkyl group, an aryl group, an aralkyl group or a blocking group and M is methyl or ethyl.

The present invention also relates to a composition for use in reducing or preventing adhesions in a patient comprising a polymer of the chemical structure:

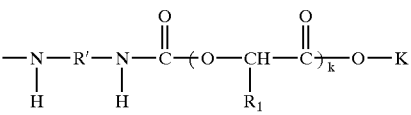

where m and k are positive integers,

R is an ethylene or propylene group with the proviso that R is not exclusively propylene when R' contains an absence of poly(ethylene oxide), R' is a $C_2$ to $C_{12}$ alkylene group, a cycloalkyl or cycloalkyl-containing group, an aryl or aryl-containing group, 4,4'-diphenylmethane, toluene, naphthalene, 4,4'-dicyclohexylmethane, cyclohexyl, 3,3'-dimethylphenyl, 3,3'-dimethyl-diphenylmethane, 4,6'-xylylene, 3,5,5-trimethylcyclohexyl, 2,2,4-trimethylhexamethylene, p-phenylene or a poly(ethylene oxide) containing or poly(ethylene oxide) rich chain and K is any group derived from a compound which is unable to initiate ring opening polymerization of a starting lactone. Preferably, K is a $C_1$ to $C_{12}$ alkyl group, an aryl group, an aralkyl group or a substituted $C_1$ to $C_{12}$ alkyl group, an aryl group, an aralkyl group, or a C=C containing group. Most preferably, K is methyl or ethyl.

The present invention also relates to a composition for use in reducing or preventing adhesions in a patient comprising a polymer of the chemical structure:

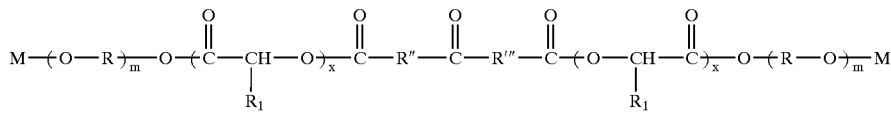

where m and x are positive integers,

R is an ethylene and/or propylene group with the proviso that R is not exclusively a propylene group when R'' and R''' contain an absence of poly(ethylene oxide), $R_1$ is a hydrogen or methyl group, R'' is a $C_0$ to $C_{12}$ alkylene group or a hydroxyl or carboxylic acid substituted alkyl group, a cycloalkyl, a hydroxyl-containing cycloalkyl, or cycloalkyl-containing group, an aryl or aryl-containing group, or a polyoxyalkylene chain-containing group comprised of poly(ethylene oxide), poly(ethylene oxide)-co-poly(propylene oxide) or a poly(ethylene oxide) rich chain, R''' is selected from the group consisting of poly(ethylene oxide), poly(ethylene oxide)-co-poly(propylene oxide), a poly(ethylene oxide)-rich chain, a diol, a diamine, a dicarboxylic acid and an ABA triblock, said diol preferably being selected from the group consisting of ethylene glycol, butanediol, OH-terminated polycaprolactone, poly(propylene glycol), OH-terminated polyester or oligoesters and tartaric acid, said diamine being preferably selected from the group consisting of ethylene diamine, hexamethylene diamine, amino acids, and oligopeptides and said dicarboxylic preferably being selected from the group consisting of succinic acid, sebacic acid, adipic acid, malic acid, oxalic acid, maleic acid, fumaric acid, COOH-terminated polycaprolactone, and COOH-terminated polyesters or oligoesters, wherein A is a polyester unit and B is selected from the group consisting of poly(ethylene oxide), poly(ethylene oxide)-co-poly(propylene oxide), a poly(ethylene oxide) rich chain, a diol, a diamine and a dicarboxylic acid, $R_1$ is H or $CH_3$ and M is a non-reactive group. Preferably, the non-reactive group is a $C_1$ to $C_{12}$ alkyl group, an aryl group, an aralkyl group or a substituted $C_1$ to $C_{12}$ alkyl group, an aryl group, an aralkyl group or a blocking group and M is methyl or ethyl.

Other embodiments of the present invention are directed to a composition for use in reducing or preventing adhesions in a patient comprising a polymer of the chemical structure:

agent. Although in many preferred embodiments the B block of the ABA triblock or AB diblock is hydrophilic and will have a high degree of compatability with water, thus allowing certain of the polymeric films according to the present invention to absorb large quantities of water or dissolve in water, it is the hydrophilic chain extender or coupler used in various polymers according to the present invention which utilize hydrophobic and hydrophilic B blocks, which allows delivery of these polymer compositions in aqueous solutions. Although in the present invention the ABA triblocks and AB diblocks are preferably non-water soluble (especially, for example, in the case of films and in other aspects of the present invention), in a number of aspects of the present invention including films, or other preformed structures, and in viscous solutions, gels, dispersions and sprays, the use of ABA triblocks and AB diblocks which are substantially water soluble may be advantageous. One of ordinary skill will readily know how to modify the polymers according to the present teachings in an effort to adjust the formulations to maximize delivery within a particular treatment context.

In the present application, the following chain extenders or coupling agents find use in preparing pre-polymerized, non-preformed polymers such as gels and viscous solutions having desirable characteristics for reducing or preventing post-operative adhesion:

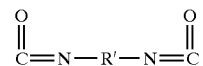

where R' is a $C_2$ to $C_{12}$, preferably a $C_2$ to $C_8$ alkylene group, a cycloalkyl or cycloalkyl-containing group, an aryl or aryl-containing group, 4,4'-diphenylmethane, toluene,

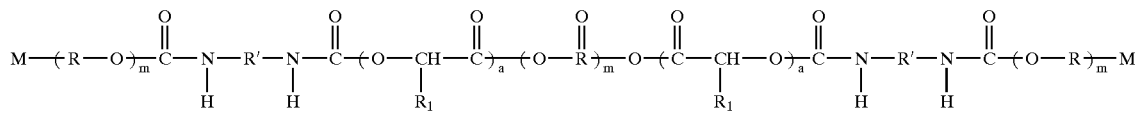

where m and a are positive integers,

R is an ethylene group and/or propylene group with the proviso that R is not exclusively a propylene group when R' contains an absence of poly(ethylene oxide), M is a non-reactive group, R' is a $C_2$ to $C_{12}$ alkylene group, a cycloalkyl or cycloalkyl-containing group, an aryl or aryl-containing group, 4,4'-diphenylmethane, toluene, naphthalene, 4,4'-dicyclohexylmethane, cyclohexyl, 3,3'-dimethylphenyl, 3,3'-dimethyl-diphenylmethane, 4,6'-xylylene, 3,5,5-trimethylcyclohexyl, 2,2,4-trimethylhexamethylene, p-phenylene, or a poly(ethylene oxide) containing or poly(ethylene oxide) rich chain, M is a non-reactive group, $R_1$ is H or $CH_3$. Preferably, the non-reactive group is a $C_1$ to $C_{12}$ alkyl group, an aryl group, an aralkyl group or a substituted $C_1$ to $C_{12}$ alkyl group, an aryl group, an aralkyl group or a blocking group and M is methyl or ethyl.

In various materials according to the present invention which are included in preformed and non-preformed materials such as films, viscous solutions, suspensions and gels, among others, the polymers may comprise ABA triblocks or AB diblocks as disclosed hereinabove, which may be chain extended, coupled and/or crosslinked using a highly water soluble/water dispersible chain extender or crosslinking naphthalene, 4,4'-dicyclohexylmethane, cyclohexyl, 3,3'-dimethylphenyl, 3,3'-dimethyl-diphenylmethane, 4,6'-xylylene, 3,5,5-trimethylcyclohexyl, 2,2,4-trimethylhexamethylene or p-phenylene. Equivalents of diisocyanates may also be used as chain extenders in the present invention. Preferred chain extenders may include water soluble macrodiisocyanates including isocyanate terminated poly(oxyalkylene) diisocyanates or isocyanate-terminated polymers comprising poly(ethylene oxide), polyethylene oxide)-co-poly(propylene oxide) and poly(ethylene oxide) containing and poly(ethylene oxide) rich schains, which may be water-soluble or non-water soluble, among others.

Additional preferred chain extenders for use in the present invention include, example those according to the formula:

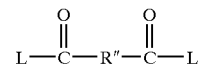

where R" is a $C_0$ to $C_{12}$, preferably a $C_2$ to $C_8$, alkylene group or a hydroxyl or carboxylic acid substituted alkylene group, alkene, a cycloalkyl, hydroxyl or carboxylic acid containing cycloalkyl or cycloalkyl-containing group, an aryl or aryl-containing group or a poly(oxyalkylene) chain comprised of poly(ethylene oxide), poly(ethylene oxide)-co-poly(propylene oxide) or other poly(ethylene oxide) containing or poly(ethylene oxide) rich chains [i.e., where poly(ethylene oxide) is included in an amount ranging from at least about 50% by weight of the polymeric chain and] L is hydroxyl, a halide such as Cl, I or Br or an ester group which can be prepared from a hydroxyl group such as an alkyl, phenyl, benzyl or substituted alkyl, phenyl or benzyl group, include activated ester groups such as a tosyl group, mesyl group or related activated groups. It is noted that diacids according to this aspect of the present invention may also find use as B blocks in certain ABA triblocks and AB diblocks according to the present invention.

It is noted that in choosing ABA triblocks or AB diblocks for formulating viscous solutions and gels according to the present invention, care must be given to providing a good balance of strength/structural integrity and biodegradability from the A block, hydrophilicity/anti-adhesion activity from the B block and further hydrophilicity in the form of water solubility/water dispersibility from the chain extender, coupling agent and/or crosslinking agent, where such agent is used. Notwithstanding certain of the embodiments previously discussed, in the present invention, non-water soluble triblocks or diblocks such as are utilized in film applications according to the present invention also may be advantageously employed in viscous solution/gel applications.

The above-described chemical formulas provide insight into the chain extended and crosslinked polymers which are used in the present invention. In the case of polymers which are preferably used in non-preformed polymers such as gels, dispersions, sprays and/or viscous solutions according to the present invention, the ultimate polymeric composition is preferably water soluble/dispersible and the polymers are preferably chain extended or crosslinked utilizing hydrophilic chain extenders or crosslinking agents, for example, diisocyanate terminated poly(alkylene glycol) chains comprising a central polyalkylene glycol chain such as poly(ethylene oxide), capped by two diisocyanate compounds, among numerous others. Examples include the use of poly(ethylene glycol) chains with a molecular range between 200 and 20,000, hexamethylene diisocyanate or a related diisocyanate as previously described being the diisocyanate. By employing non-water soluble or water soluble ABA triblocks or AB diblocks and preferably employing water soluble/dispersible chain extenders and/or crosslinking agents, polymer compositions which are used in viscous solution and gel applications provide favorable strength and structural integrity, biodegradability (the rate of which may be influenced by the length and hydrophobicity of the A block and the overall hydrophilicity of the polymer), flexibility and anti-adhesion activity from the PEG segments in the polymer and water solubility/dispersibility from the selective chain extenders which are used.

In addition to being useful for substantially reducing or preventing adhesions, the present polymers may also be used to deliver bioactive compositions to a site of activity within the patient's body. This aspect of the present invention is secondary to the anti-adhesion characteristics of the inventive polymers. It is particularly advantageous that the present polymers may be used to deliver bioactive agents which may serve to enhance the healing of the wounds created by a surgical procedure, a disease state or other condition associated with the tissue to be treated.

Exemplary bioactive agents which may be delivered pursuant to the methods according to the present invention include, for example, anticoagulants, for example heparin and chondroitin sulphate, fibrinolytics such as tPA, plasmin, streptokinase, urokinase and elastase, steroidal and non-steroidal anti-inflammatory agents such as hydrocortisone, dexamethasone, prednisolone, methylprednisolone, promethazine, aspirin, ibuprofen, indomethacin, ketoralac, meclofenamate, tolmetin, calcium channel blockers such as diltiazem, nifedipine, verapamil, antioxidants such as ascorbic acid, carotenes and alpha-tocopherol, allopurinol, trimetazidine, antibiotics, especially noxythiolin and other antibiotics to prevent infection, prokinetic agents to promote bowel motility, agents to prevent collagen crosslinking such as cis-hydroxyproline and D-penicillamine, and agents which prevent mast cell degranulation such as disodium chromolglycate, among numerous others.

In addition to the above agents, which generally exhibit favorable pharmacological activity related to promoting wound healing, reducing infection or otherwise reducing the likelihood that an adhesion will occur, other bioactive agents may be delivered by the polymers of the present invention include, for example, amino acids, peptides, proteins, including enzymes, carbohydrates, antibiotics (treat a specific microbial infection), anti-cancer agents, neurotransmitters, hormones, immunological agents including antibodies, nucleic acids including antisense agents, fertility drugs, psychoactive drugs and local anesthetics, among numerous additional agents.

The delivery of these agents will depend upon the pharmacological activity of the agent, the site of activity within the body and the physicochemical characteristics of the agent to be delivered, the therapeutic index of the agent, among other factors. One of ordinary skill in the art will be able to readily adjust the physicochemical characteristics of the present polymers and the hydrophobicity/hydrophilicity of the agent to be delivered in order to produce the intended effect. In this aspect of the invention, bioactive agents are administered in concentrations or amounts which are effective to produce an intended result. It is noted that the chemistry of polymeric composition according to the present invention can be modified to accommodate a broad range of hydrophilic and hydrophobic bioactive agents and their delivery to sites in the patient.

Synthesis of Polymers According to the Present Invention

In general, the synthesis of the present polymers proceeds by first synthesizing an ABA triblock or AB diblock. In this general reaction, a pre-prepared poly(oxyalkylene) B block (which can be purchased or synthesized from an initiating diol and an excess of an appropriate epoxide depending upon the length of the block desired) is preferably reacted with a hydroxyacid or its cyclic dimer to produce the low molecular weight ABA triblock or AB diblock. Essentially, the poly(oxyalkylene) block which is generally endcapped with hydroxyl groups or, in the case of an AB diblock is capped at one end with a hydroxyl group and at the other end with a non-reactive group, reacts with the hydroxyacid or its cyclic dimer to produce an ABA triblock or AB diblock which is end-capped with a hydroxyl group or other group(s).

Once the ABA triblock or AB diblock is formed, the hydroxyl groups at the end(s) of the molecule are reacted with difunctional chain extenders or couplers, for example, diisocyanates. This reaction produces a chain extended polymer which is readily used to prepare films and various related structures, gels, dispersions, suspensions, and viscous solutions of the present invention. In the case of certain polymers, these are of sufficiently low molecular weight so that they are in liquid form without the need to add additional solvent.

Generally, during the first stage of the reaction in which the low molecular weight ABA triblock or AB diblock is formed, the overall molecular weight and the length of the different segments will be determined by the molecular weight of the poly(oxyalkylene) block chosen to initiate the reaction, by the number of moles of hydroxyacid, its cyclic dimer or related compounds, which is reacted with the poly(oxyalkylene) block and the catalyst and various experimental parameters such as the heat and the reaction time. Thereafter, the ABA triblock or AB diblock is chain extended, coupled and/or crosslinked to produce polymers containing ABA triblocks or AB diblocks.

A preferred synthesis of the present polymers involves the use of the cyclic ester or lactone of lactic acid and glycolic acid. The use of lactide or glycolide as the reactant will enhance the production of ABA triblocks or AB diblocks which have relatively narrow molecular weight distributions and low polydispersity.

In this preferred method, lactide or glycolide (the cyclic dimer of lactic acid or glycolic acid, respectively), rather than lactic acid or glycolic acid, is first used to synthesize the ABA triblock or AB diblock from the starting poly (oxyalkylene) block. Once the triblock or diblock is obtained, the hydroxyl end-capped triblock or diblock is reacted with a diisocyanate, preferably hexamethylene diisocyanate.

The synthesis of the ABA triblock or Ab diblock preferably proceeds by way of a ring-opening mechanism, whereby the ring opening of the lactide or glycolide is initiated by the hydroxyl end groups of the PEG chain under the influence of a tin catalyst (stannous octoate). An ABA type triblock or AB type diblock is generated at this point, the molecular weight of which is a function of both the molecular weight of the central PEG chain and the length of the PLA lateral block(s). Typically, the molecular weight of the triblock spans between about 4,000 to about 30,000 (but may be as low as 1,000 or less and as high as 250,000 or more). In the case if the diblock, the molecular weight may range as low as several hundred to upwards of 50,000 or more. After synthesis of the ABA triblock or ABA diblock, the final polymer is preferably obtained by chain extending the hydroxyl terminated triblocks with difunctional reactants such as isocyanates, most preferably hexamethylene diisocyanate.

The chemical and physical properties of the different polymers will vary as a function of different parameters, the molecular weight of the PEG and PLA segments along the backbone being of particular importance.

The preferred method has several advantageous characteristics including:

1. a rapid, nearly quantitative reaction which is complete in from 1 to 3 hours;
2. the reaction takes place under moderate reaction conditions (140° C.) thus minimizing side reactions;
3. the resulting triblock or diblock contains an extremely narrow polydispersity (P=1.3–1.4 or better; and
4. the triblock or diblock contains little or no homopolymer.

Preparation of Adhesion Barrier Structures

Barrier structures (which term includes films as well as cylinders and related three-dimensional structures) for use in the present invention are prepared by first producing the polymer according to the present invention and then dissolving the polymer in a solvent, such as chloroform, methylene chloride or a related organic solvent. Films, for example, are preferably prepared by placing the solution containing polymer in a mold or a related receptable and then allowing the solvent to evaporate. The resulting film is homogeneous and of uniform thickness and density. The film may be used as prepared or cut into segments for application to a desired site in a patient. In addition to the above-described solvent cast method, a continuous solvent cast process, a thermal cast method or related methods well known in the art may be used to make films and other structures according to the present invention.

In order to prepare other three dimensional structures of polymer, such as cylinders and related shapes, these may be cast or molded using various techniques, starting with solid polymer. Methods to produce these structures using these techniques are well known in the art.

Preparation of Gels, Viscous Solutions and Dispersions

In order to prepare the gels, viscous solutions and dispersions according to the present invention, polymer in powder, flakes or other related form is dissolved or suspended in an aqueous solution, preferably sterile isotonic saline solution, generally at room temperature and then mixed in the solution to produce the final gel, viscous solution or dispersion. Viscosity of the system is readily adjusted by adding further polymer or aqueous solution. The gels, viscous solutions and dispersions are utilized under sterile conditions.

While not being limited by way of theory, it is believed that the chain extended polymers of the present invention form integral layers in films, gels or viscous solutions when applied to tissue for surgical applications. The resulting integral polymers provide an excellent barrier which substantially reduces the formation of post-operative adhesions.

Having generally described the invention, reference is now made to the following examples intended to illustrate preferred embodiments and comparisons but which are not to be construed as limiting to the scope of this invention as more broadly set forth above and in the appended claims.

EXAMPLES

Example 1

Effect of Polymer Films on Adhesion

The purpose of this experiment was to test the efficacy of EO/LA films (ratios 2.5, 3.3, and 4.0) on the formation of adhesions in a rabbit model of adhesion formation between the sidewall and the bowel.

Materials and Methods

Animals

Twenty female New Zealand rabbits, 2.4–2.7 kg, were purchased and quarantined for at least 2 days prior to use. The rabbits were housed on a 12:12 light: dark cycle with food and water available ad libitum.

Synthesis of Materials

The synthesis of the polymers can be summarized as follows:

1. ABA triblock was synthesized as follows:

Polyethylene glycol (MW=6,000) was dried in vacuo overnight at 80° C. Thereafter, the PEG was cooled down to room temperature, the vacuum was broken by flushing dry $N_2$ through the system and lactide is thereafter added in an appropriate amount (depending upon the length of the A block desired). The mixture of PEG and lactide is placed in an oil bath at 140° C. and after 2–3 minutes (which is generally required to homogenize the system), stannous octoate is added (the catalyst/lactide mole ratio is 1/400). The mixture is then flushed with $N_2$ for a period of about 5 minutes, whereupon the $N_2$ is removed and the flask containing PEG and lactide is then capped and stirred at 140° C. in an oil bath for 2 hours. At the end of a 2 hour period, the mixture is removed from the oil bath, allowed to cool, dissolved in chloroform and precipitated in ether. The precipitate is thereafter collected and dried overnight in vacuo at 50° C. It is then solubilized in chloroform and the chloroform is evaporated to form a film of approximately 10 mil thickness.

2. The Polymer was synthesized as follows:

The synthesis of the polymers is completed by chain extending the ABA triblocks by reacting their hydroxyl-terminated groups with diisocyanates, typically hexamethylene diisocyanate (HDI). The triblock obtained above is dried at 80° C. in vacuo for a period of two hours. After the two hour period, vacuum is broken by flushing $N_2$ through the system and a minimal amount of dry dioxane to dissolve the triblock is added. The required amount of catalyst is dissolved in dioxane (about 5 ml) and added to the triblock. 15 ml of dry dioxane is introduced into a separatory funnel and the required amount of HDI is added (the HDI:catalyst molar ratio is 5:1, and the HDI is in a 7% molar excess respective to the triblock—the typical Triblock:HDI:Catalyst molar ratios are, therefore, 1.0:1.07:0.2, respectively). Once the triblock is fully dissolved, the HDI solution is added dropwise (over a period of 30 minutes) to the triblock solution. A condensor is then connected to the reaction flask to prevent dioxane loss and the reaction is continued for a period of 2.5 hours. After 2.5 hours, the reaction is removed from the oil bath, allowed to cool and the polymer solution is precipitated with ether. The precipitated polymer is then collected and dried overnight at 50° C. The material is then solubilized in chloroform and the chloroform is evaporated (room temperature overnight followed by 5 hours under vacuum at 40° C.) to form a film of approximately 10 mil thickness.

The final polymers used in this experiment had EO/LA ratios of 2.5, 3.3 and 4.0.

Materials: The above-obtained films were used in the following experiments. The sutures used were as follows: 6-0 Prolene (Ethicon, Raritan, NJ) was used to tack the film in place and 3-0 coated Dexon II suture (Davis and Geck, Manati, PR) was used to close the peritoneum and skin.

Sidewall Model: Rabbits were anesthetized with a mixture of 55 mg/kg ketamine hydrochloride and 5 mg/kg Rompun intramuscularly. Following preparation for sterile surgery, a midline laparotomy was performed. The cecum and bowel were exteriorized and digital pressure was exerted to create subserosal hemorrhages over all surfaces. The damaged intestine was then lightly abraded with 4" 4×4 ply sterile gauze until punctate bleeding was observed. The cecum and bowel was then returned to its normal anatomic position. A 3×3 $cm^2$ area of peritoneum and transversus abdominous muscle was removed on the right lateral abdominal wall. The prepared film (see below) was sutured in place using 6-0 prolene at 6 sites (at each corner and in the center of the side of the film on two sides). After 31–32 days, the rabbits were terminated and the percentage of the area of the sidewall injury that was involved in adhesions was determined. In addition, the tenacity of the adhesions was scored using the following system:

0=No adhesions

1=mild, easily dissectable adhesions

2=moderate adhesions, non-dissectable, does not tear the organ

3=dense adhesions, non-dissectable, tears organ when removed

A reduction in either the area or the tenacity of the adhesions was considered to be beneficial.

Preparation of Film: The films were stored at room temperature in a desiccator until the day of surgery. On the day of surgery, the film was cut to 3 cm×3 cm in sterile conditions. Ten to 12 minutes prior to placement, the film was placed in sterile, double distilled water to allow hydration. During hydration, the films went from opaque to clear and increased in size proportionate to the EO/LA ratio (the higher the ratio the more the increase). Thereafter, the film was rinsed with phosphate buffered saline (pH 7.4) to restore isotonicity to the surface. Just prior to placement, the film was blotted on sterile gauze to remove excess moisture.

RESULTS: During the early postoperative interval, two rabbits died. Coincidentally, both received the film of the 3.3 ratio. Postmortem necropsy revealed nothing unusual and the deaths were attributed to the surgical procedure. No inflammation was noted intraperitoneally.

One rabbit from the group that received the film with the ratio 2.5 was sacrificed 13 days later. Some material was present at the site (identity unknown). One rabbit from the group that received the film with the ratio 4.0 died 24 days after surgery. No reason for the mortality was noted upon necropsy.

One month after surgery, the remaining rabbits were sacrificed and the degree of adhesion formation determined (Table 1). At surgery, 5 rabbits were controls. However, at necropsy, 6 rabbits had been given control numbers with two rabbits given the same number (1-2 on the surgery day). One number from the group that had film with the ratio 4.0 was missing (2-1 from surgery day). Of the rabbits that were confirmed as controls (4 of the 6), 3 had adhesions (one with 80% and 2 with 100% of the area of the sidewall injury with adhesions). In all of these rabbits, the tenacity of the adhesions was 3+. All of the rabbits with films placed at surgery had no adhesions at necropsy. Of the two rabbits with the same number, one had 100% of the sidewall injury area covered with 3+ adhesions and the other had no adhesions at the site of injury.

DISCUSSION: The films made from various ratios of EO/LA were highly efficacious at the reduction of adhesion formation. In the control rabbits which had surgery and the sutures placed in the same pattern as that in the treated rabbits, the majority (60%, 75% or 80% depending upon the inclusion of the mismarked rabbit) of the rabbits had the formation of severe, cohesive adhesions at the site of sidewall injury. In the rabbits that were confirmed to have been given the film, all rabbits had no adhesions at the site of adhesion formation. At two weeks and later, the site of injury appeared fully healed.

TABLE 1

| | Area of Adhesion Formation at Site of Sidewall Injury % Area Involved | | | | |
|---|---|---|---|---|---|
| Treatment | 0 | 1–25 | 26–50 | 51–75 | 76–100 |
| Surgical Control n = 4 | 20* | 0 | 0 | 0 | 75 |

TABLE 1-continued

Area of Adhesion Formation at Site of Sidewall Injury
% Area Involved

| Treatment | 0 | 1–25 | 26–50 | 51–75 | 76–100 |
|---|---|---|---|---|---|
| EO/LA Ratio 2.3 n = 4 | 100 | 0 | 0 | 0 | 0 |
| EO/LA Ratio 3.3 n = 3 | 100 | 0 | 0 | 0 | 0 |
| EO/LA Ratio 4.0 n - 3 | 100 | 0 | 0 | 0 | 0 |

* 1 out of 5 animals had no adhesions.

It is to be understood that the examples and embodiments described hereinabove are for the purposes of providing a description of the present invention by way of example and are not to be viewed as limiting the present invention in any way. Various modifications or changes that may be made to that described hereinabove by those of ordinary skill in the art are also contemplated by the present invention and are to be included within the spirit and purview of this application and the following claims.

What is claimed is:

1. A composition for use in reducing or preventing adhesions in a patient comprising a polymer of the chemical structure:

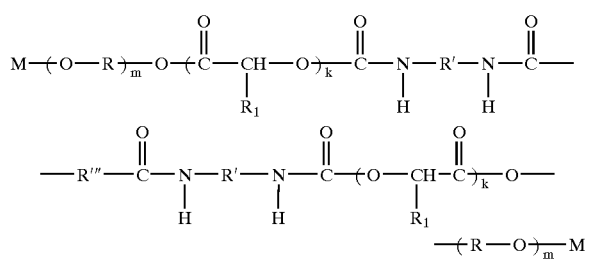

where m and k are positive integers,

R is an ethylene group or a propylene group with the proviso that R is not exclusively a propylene group when R' and R'" contain an absence of poly(ethylene oxide), R' is a $C_2$ to $C_{12}$ alkylene group, a cycloalkyl or cycloalkyl-containing group, an aryl or aryl-containing group, 4,4'-diphenylmethane, toluene, naphthalene, 4,4'-dicyclohexylmethane, cyclohexyl, 3,3'-dimethylphenyl, 3,3'-dimethyl-diphenylmethane, 4,6'-xylylene, 3,5,5-trimethylcyclohexyl, 2,2,4-trimethylhexamethylene, p-phenylene or a poly(ethylene oxide) containing or poly(ethylene oxide) rich chain, R'" is selected from the group consisting of poly(ethylene oxide), poly(ethylene oxide)-co-poly(propylene oxide), a poly(ethylene oxide)-rich chain, a diol, a diamine, a dicarboxylic acid or an ABA triblock, wherein A is a polyester unit and B is selected from the group consisting of poly(ethylene oxide), poly(ethylene oxide)-co-poly(propylene oxide), a poly(ethylene oxide)-rich chain, a diol, a diamine, and a dicarboxylic acid, $R_1$ is H or $CH_3$ and M is a substituted or unsubstituted $C_1$ to $C_{12}$ alkyl group, aryl group, aralkyl group or is a blocking group, said polymeric composition having an EO/LA ratio which falls within the range of about 0.1 to about 100.

2. The method according to claim 1 wherein said diol is selected from the group consisting of ethylene glycol, butanediol, OH-terminated polycaprolactone, poly(propylene glycol), OH-terminated polyester or oligoesters, tartaric acid, said diamine is selected from the group consisting of ethylene diamine, hexamethylene diamine, amino acids, and oligopeptides and said dicarboxylic acid is selected from the group consisting of succinic acid, sebacic acid, adipic acid, malic acid, oxalic acid, maleic acid, fumaric acid, COOH-terminated polycaprolactone, and COOH-terminated polyesters or oligoesters.

3. The composition according to claim 1 where M is methyl or ethyl.

4. The composition according to claim 1 wherein R is exclusively an ethylene group.

5. The composition according to claim 1 wherein M is a $C_1$ to $C_{12}$ alkyl group.

6. The composition according to claim 1 wherein R' is a 2,2,4-hexamethylene group.

7. The composition according to claim 1 wherein R'" is a poly(ethylene oxide) group.

8. The composition according to claim 2 wherein R is exclusively an ethylene group.

9. The composition according to claim 2 wherein M is a $C_1$ to $C_{12}$ alkyl group.

10. The composition according to claim 2 wherein R' is a 2,2,4-hexamethylene group.

11. The composition according to claim 2 wherein R'" is a poly(ethylene oxide) group.

* * * * *